(12) United States Patent
Hillman et al.

(10) Patent No.: US 6,200,790 B1
(45) Date of Patent: Mar. 13, 2001

(54) VESICLE TRANSPORT ASSOCIATED PROTEINS

(75) Inventors: Jennifer L. Hillman, Mountain View; Preeti Lal, Santa Clara; Purvi Shah, Sunnyvale; Neil C. Corley, Mountain View, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/368,402

(22) Filed: Aug. 4, 1999

Related U.S. Application Data

(62) Division of application No. 09/193,510, filed on Nov. 17, 1998, now Pat. No. 5,981,226, which is a division of application No. 08/948,616, filed on Oct. 10, 1997, now Pat. No. 5,840,539.

(51) Int. Cl.$^7$ ..................................................... C12N 9/14
(52) U.S. Cl. .............................. 435/195; 530/350; 435/4; 435/7.1; 435/547; 435/548
(58) Field of Search ................................. 530/350; 435/4, 435/7.1, 195, 547, 548

(56) References Cited

U.S. PATENT DOCUMENTS

| | | | |
|---|---|---|---|
| 5,688,936 | 11/1997 | Edwards et al. | 536/23.5 |
| 5,834,241 | 11/1998 | Hillman et al. | 435/69.1 |

OTHER PUBLICATIONS

Rothman, J.E., et al., "Protein Sorting by Transport Vesicles", *Science*, 272:227–234 (1996).

Newman, A.P., et al., "Bos1p, a membrane protein required for ER to Golgi transport in yeast, co–purifies with the carrier vesicles and with Bet1p and the ER membrane", *The EMBO Journal*, 11: 3609–3617 (1992).

Hay, J.C., et al., "Mammalian Vesicle Trafficking Proteins of the Endoplasmic Reticulum and Golgi Apparatus", *The Journal of Biological Chemistry*, 271: 5671–5679 (1996).

Dascher, C., et al., "Identification and Structure of Four Yeast Genes (SLY) That Are Able To Suppress the Functional Loss of YPT1, a Member of the RAS Superfamily", *Molecular and Cellular Biology*, 11: 872–885 (1991).

Nakano, K, et al., "Isolation and sequencing of two cDNA clones encoding Rho proteins from the fission yeast *Schizosaccharomyces pombe*", *Gene*, 155: 119–122 (1995). (GI 1064855) (GI 1064856).

Murphy, C., et al., "Endosome dynamics regulated by a Rho protein", *Nature*, 384: 427–432 (1996).

Xu, Y., et al., (GI 2316079) GenBank Sequence Database (Accession AF003999) National Center for Biotechnology Information: National Library of Medicine, Bethesda, Maryland 20849. (GI 2316080) No Date Provided.

Zhang, T., et al., (GI 2253427) GenBank Sequence Database (Accession AF007552), National Center for Biotechnology Information: National Library of Medicine, Bethesda, Maryland 20849. (GI 2253428) No Date Provided.

Hay, J.C., et al., (GI 1223893) GenBank Sequence Database (Accession U42209), National Center for Biotechnology Information: National Library of Medicine, Bethesda, Maryland 20849. (GI 1223894) No Date Provided.

Murphy, C., et al., (GI 1702942) GenBank Sequence Database (Accession X84325), National Center for Biotechnology Information: National Library of Medicine, Bethesda, Maryland 20849. (GI 1702943) No Date Provided.

Shimizu, F., et al., "Isolation of a novel human cDNA (rhoHP1) homologous to rho genes", *Biochimica et Biophysica Acta*, 1351: 13–16 (1997). (GI 1944384) (GI 1944385).

Xu, X. et al., "GS15, a 15–Kilodalton Golgi Soluble N–Ethylmaleimide–sensitive Factor Attachment Protein Receptor (SNARE) Homologous to rbet 1*", *The Journal of Biological Chemistry*, 272(32): 20162–20166 (1997).

Xu, Y., et al., (GI 2316077) GenBank Sequence Database (Accession AF003998) National Center for Biotechnology Information: National Library of Medicine, Bethesda, Maryland 20849. (GI 2316078) No Date Provided.

*Primary Examiner*—Ponnathapau Achutamurthy
*Assistant Examiner*—Bradley S. Mayhew
(74) *Attorney, Agent, or Firm*—Incyte Genomics, Inc.

(57) ABSTRACT

The invention provides human vesicle transport associated proteins (VTAP) and polynucleotides which identify and encode VTAP. The invention also provides expression vectors, host cells, agonists, antibodies and antagonists. The invention also provides methods for treating disorders associated with expression of VTAP.

7 Claims, 19 Drawing Sheets

```
                              9                 18              27              36              45              54
5' NNG   GCC   ACG   TCT   GAG   GCG   GCT   GTG   GCC   GCG   TGC   GGT   GTC   CGC   GTC   GAG   GAG   CCG 63                72              81              90              99              108
GGG   CAG   GGC   ACG   ATG   GCG   GAC   TGG   GCT   CGG   GCT   CAG   AGC   CCG   GGC   GCT   GTG   GAA
                    M     A     D     W     A     R     A     Q     S     P     G     A     V     E 117               126             135             144             153             162
GAG   ATT   CTA   GAC   CGG   GAG   AAC   AAG   CGA   ATG   GCT   GAC   AGC   CTG   GCC   TCC   AAA   GTC
E     I     L     D     R     E     N     K     R     M     A     D     S     L     A     S     K     V 171               180             189             198             207             216
ACC   AGG   CTC   AAA   TCG   CTC   GCC   CTG   GAC   ATC   GAT   AGG   GAT   GCA   GAG   GAT   CAG   AAC
T     R     L     K     S     L     A     L     D     I     D     R     D     A     E     D     Q     N 225               234             243             252             261             270
CGG   TAC   CTG   GAT   GGC   ATG   GAC   TCG   GAT   TTC   ACA   AGC   ATG   ACC   AGC   CTG   CTT   ACA
R     Y     L     D     G     M     D     S     D     F     T     S     M     T     S     L     L     T
```

FIGURE 1A

```
                    279            288            297        306            315            324
GGG AGC GTG AAG CGC TTT TCC ACA ATG GCA AGG TCC GGA CAA GAC AAC CGG AAG
 G   S   V   K   R   F   S   T   M   A   R   S   G   Q   D   N   R   K 333            342            351        360            369            378
CTT CTA TGT GGC ATG GCC GTG GGT CTA ATT GTG GCC TTC TTC ATC CTC TCC TAC
 L   L   C   G   M   A   V   G   L   I   V   A   F   F   I   L   S   Y 387            396            405        414            423            432
TTC TTG TCC AGG GCA AGG ACG TGA AGC GGG AGT GGG AGC TGG TGT CTG TGG GTG CCA
 F   L   S   R   A   R   T 441            450            459        468            477            486
AGG GCA GCC AGG GTC TTC CCT GCC TGG TGT TTT GGG CTC CAG AGG ACT TAC CTA 495            504            513        522
CAA AAT ACT CCT TTG CAA TTA TAA AAA AAA AAA AAA AAA AAA A 3'
```

FIGURE 1B

```
                                                        45          54
5'- CGG AAT TCG GCT CGA GGT CTC GAC AGG TTT TCT CTG TTG GTT GAA ATG TCT ATG
                                                                     M   S   M
                                                        99          108
    ATT TTA TCT GCC TCA GTC ATT CGT ATT CGT GTC AGA GAT GGA CTG CCA CTT TCT GCT TCT
    I   L   S   A   S   V   I   R   V   R   D   G   L   P   L   S   A   S
                                                        153         162
    ACT GAT TAT GAA CAA ACA GGA AGC ACA ATG CAG GAG TGC AGA AAG TAT TTT AAA ATG
    T   D   Y   E   Q   T   G   S   T   M   Q   E   C   R   K   Y   F   K   M
                                                        207         216
    CTT TCG AGG AAA CTT GCT CAA CTT CCT GAT AGA TGT ACA CTG AAA ACT GGA CAT
    L   S   R   K   L   A   Q   L   P   D   R   C   T   L   K   T   G   H
                                                        261         270
    TAT AAC ATT AAT TTT ATT AGC TCT CTG GGA GTG AGC TAC ATG TTG TGC ACT
    Y   N   I   N   F   I   S   S   L   G   V   S   Y   M   L   C   T
                                                        315         324
    GAA AAT TAC CCA AAT GTT CTC GCC TTC TCT TTC CTG GAT GAG CTT CAG AAG GAG
    E   N   Y   P   N   V   L   A   F   S   F   L   D   E   L   Q   K   E
```

FIGURE 2A

```
       333         342         351         360         369         378
TTC ATT ACT ACT TAT AAC ATG ATG AAG ACA AAT ACT GCT GTC AGA CCA TAC TGT
 F   I   T   T   Y   N   M   M   K   T   N   T   A   V   R   P   Y   C 387         396         405         414         423         432
TTC ATT GAA TTT GAT AAC TTC ATT CAG AGG ACC AAG CAG CGA TAT AAT AAT CCC
 F   I   E   F   D   N   F   I   Q   R   T   K   Q   R   Y   N   N   P 441         450         459         468         477         486
AGG TCT CTT TCA ACA AAG ATA AAT CTT TCT GAC ATG CAG ACG GAA ATC AAG CTG
 R   S   L   S   T   K   I   N   L   S   D   M   Q   T   E   I   K   L 495         504         513         522         531         540
AGG CCT TAT CAA ATT TCC ATG TGC GAA CTG GGG TCA GCC AAT GGA GTC ACA
 R   P   Y   Q   I   S   M   C   E   L   G   S   A   N   G   V   T 549         558         567         576         585         594
TCA GCA TTT TCT GTT GAC TGT AAA GGT GCT GGT AAG ATT TCT TCT GCT CAC CAG
 S   A   F   S   V   D   C   K   G   A   G   K   I   S   S   A   H   Q 603         612         621         630         639         648
CGA CTG GAA CCA GCA ACT CTG TCA GGG ATT GTA GGA TTT ATC CTT AGT CTT TTA
 R   L   E   P   A   T   L   S   G   I   V   G   F   I   L   S   L   L
```

FIGURE 2B

```
         657                666         675         684         693         702
TGT GGA GCT CTG AAT TTA ATT CGA GGC TTT CAT GCT ATA GAA AGT CTC CTG CAG
 C   G   A   L   N   L   I   R   G   F   H   A   I   E   S   L   L   Q 711                720         729         738         747         756
AGT GAT GGT GAT GAT TTT AAT TAC ATT GCA TTT TTC CTT GGA ACA GCA GCC
 S   D   G   D   D   F   N   Y   I   A   F   F   L   G   T   A   A 765                774         783         792         801         810
TGC CTT TAC CAG TGT TAT TTA CTT GTC TAC TAC ACC GGC TGG CGG AAT GTC AAA
 C   L   Y   Q   C   Y   L   L   V   Y   Y   T   G   W   R   N   V   K 819                828         837         846         855         864
TCT TTT TTG ACT TTT GGC TTA ATC TGT CTA TGC AAC ATG TAT CTC TAT GAA CTG
 S   F   L   T   F   G   L   I   C   L   C   N   M   Y   L   Y   E   L 873                882         891         900         909         918
CGC AAC CTC TGG CAG CTT TTC TTT CAT GTG ACT GTG GGA GCA TTT GTT ACA CTA
 R   N   L   W   Q   L   F   F   H   V   T   V   G   A   F   V   T   L 927                936         945         954         963         972
CAG ATC TGG CTA AGG CAA GCC CAG AAG GCT CCC GAT TAT GAT GTC TGA CAC
 Q   I   W   L   R   Q   A   Q   K   A   P   D   Y   D   V   *   H 981                990         999         1008        1017        1026
CAT CCT TCA GAT CTA TTG CCT TGG CTT CAG GGG GAT AAG GAG GGA ACA TAT CAT
```

FIGURE 2C

```
           1035           1044           1053           1062           1071           1080
AAC TGC ACT GTG ATG AAG AAG CTG TTC CCC ACA GAG GAG AAG CTC TGC TTT CTT
           1089           1098           1107           1116           1125           1134
TCT CTC CAA CTT TCC TTT TTT AAA ATC AGC ATG ATG TGC CTG TGA GCA TGG AAG
           1143           1152           1161           1170           1179           1188
AGT CCT CTC AGA AGA ATG TTG GCC ATG AGA CTA TCA TTC AGA GGA GGA GGG GAT
           1197           1206           1215           1224           1233           1242
TTC TCT CTT CAA GGC CAT AAC AGT GGA AGA ACA GTC ATA TGC CAT TGG AAG TCT
           1251           1260           1269           1278           1287           1296
TGG CCA GTC CTG AAT CCT TCC TGA AGA GTT CAG AAA ATA GAT GTG GTA TTG
           1305           1314           1323           1332           1341           1350
CTC TGA GGA CCA GGC AGG AAC TCT ACA ACC TGA GTT TGC CTT TGT GAG GCA
           1359           1368           1377           1386           1395           1404
TTA GTA TAG ACC AAA TAA AAA GCT GCA GAA ATT GGA AAG TTT ATG TTT TAA ATA
           1413           1422
AAT GAC TGT GAT AAA TAT C 3'
```

FIGURE 2D

```
                                 9                 18            27            36            45            54
5' NGG   TCT   CTG   CGC   CGC   AGC   CGC   CCC   GCC   TCA   GCG   CCC   GGC   CCC   GGG   ATG
                                                                                                M 63                72            81            90            99           108
   ACG   GCG   GCC   CAG   GCC   GCG   GGT   GAG   GAG   GCG   CCA   GGC   GTG   TCC   GTC   AAG
   T     A     A     Q     A     A     G     E     E     A     P     P     G     V     S     V     K 117              126           135           144           153           162
   GTG   GTC   CTG   GTG   GGC   GAC   GGC   GGC   TGC   GGG   AAG   TCG   ACG   CTG   ATG   GTC   TTC
   V     V     L     V     G     D     G     G     C     G     K     S     T     L     M     V     F 171              180           189           198           207           216
   GCC   GAT   GGG   GCC   TTC   CCC   GAG   AGC   TAC   ACC   CCC   ACG   GTG   TTT   GAG   CGG   TAC   ATG
   A     D     G     A     F     P     E     S     Y     T     P     T     V     F     E     R     Y     M 225              234           243           252           261           270
   GTC   AAC   CTG   CAA   GTG   AAA   GGC   AAA   GGC   TAC   AGC   CCT   GTG   CAC   CTC   CAC   ATC   TGG   GAC   ACA   GCA
   V     N     L     Q     V     K     G     K     G     Y     S     P     V     H     L     H     I     W     D     T     A 279              288           297           306           315           324
   GGG   CAA   GAT   GAC   TAT   GAC   CGC   CTG   CGG   CCC   CTG   TCC   TAC   CCT   GAC   GCC   AGC   GTC
   G     Q     D     D     Y     D     R     L     R     P     L     S     Y     P     D     A     S     V 333              342           351           360           369           378
   CTG   CTT   TGC   TTC   GAT   GTC   ACC   AGC   CCG   AAC   AGC   TTT   GAC   AAC   ATC   TTT   AAC
   L     L     C     F     D     V     T     S     P     N     S     F     D     N     I     F     N
```

FIGURE 3A

```
          387          396          405          414          423          432
     CGG TGG TAC CCA GAA GTG AAT CAT TTC TGC AAG AAG GTA CCC ATC ATC GTC GTG
      R   W   Y   P   E   V   N   H   F   C   K   K   V   P   I   I   V   V 441          450          459          468          477          486
     GGC TGC AAG ACT GAC CTG CGC AAG GAC AAA TCA CTG GTG AAC AAG CTC CGA AGA
      G   C   K   T   D   L   R   K   D   K   S   L   V   N   K   L   R   R 495          504          513          522          531          540
     AAC GGA TTG GAG CCT GTG ACC TAC CAC AGG GGC CAG GAG ATG GCG AGG TCC GTG
      N   G   L   E   P   V   T   Y   H   R   G   Q   E   M   A   R   S   V 549          558          567          576          585          594
     GGC GTG GCC TAC CTC GAG TGC TCG GCT CGG CTC CAT GAC AAC GTC CAC GCC
      G   A   V   Y   L   E   C   S   A   R   L   H   D   N   V   H   A 603          612          621          630          639          648
     GTC TTC CAG GAG GCC GCC GAG GTG GCC CTC AGC AGC CGC GGT CGC AAC TTC TGG
      V   F   Q   E   A   A   E   V   A   L   S   S   R   G   R   N   F   W 657          666          675          684          693          702
     CGG CGG ATT ACC CAG GAG GGC TTT TGC GTG GTG ACC TGA GCG GCT CGG GTC CCA
      R   R   I   T   Q   E   G   F   C   V   V   T   *   A   A   R   V   P 711          720          729          738          747          756
     GCG ACG CGG GAA GGG GCA GGG CGC CGC TGA CCT GCT GCT GAG CTG GCT GGG CTG GAC
```

FIGURE 3B

```
              765        774       783       792        801       810
    CCG GTC CCT AGG CTG TGA CCG CCG AAC TCC ACT GCA ACA GAC GGG CGC CAC CAA 819        828       837       846        855       864
    AGC CAG GCC CTG AGG CCT GGG AGT CCT GGA CTG AGA AAG GGG GTT CCT GGG CCC 873        882       891       900        909       918
    ACC TGC TCT GTG TAG GGC TCG TCC TGC GGT GCC CGA GAA TCA CTC GCT AAC CCC 927        936       945       954        963       972
    TAT GCC CGG TCC CGG ACC GAC ATC CTG GAG CCG CCT GTG CAG CCT GAT GCC CCC 981        990       999       1008       1017      1026
    TCG TGG CTG CTC CCA GGG CTG CAC CTG CCA GGA CCT AAT GTT CTT AGG TCC CTC 1035       1044      1053      1062       1071      1080
    TGG CCA GAA CCC ACA CCC GGC CCC TTC CCA CCT GTC ATA CTG GTA ACT GTA ACA 1089       1098
    AGA AAA ACG ACA TCA CTT A 3'
```

| LIBRARY | ABUN | LIBRARY DESCRIPTION |
|---|---|---|
| TLYJINT01 | 2 | JURKAT CELL LINE, T-CELL LEUKEMIA, M, |
| PROSTUT01 | 2 | PROSTATE TUMOR, 50 M, MATCH TO PROSNOT02 |
| BRSTNOT09 | 2 | BREAST, 45 F, MATCH TO BRSTTUT08 |
| SMCANOT01 | 1 | SMOOTH MUSCLE CELL LINE, AORTA, M |
| PROSTUT05 | 1 | PROSTATE TUMOR, 69 M, MATCH TO PROSNOT07 |
| PROSBPT03 | 1 | PROSTATE, HYPERPLASIA, 59 M |
| PENCNOT05 | 1 | PENIS, LEFT CORPUS CAVERNOSUM, M |
| LNODNOT03 | 1 | LYMPH NODE, 67 M |
| KIDNNOT19 | 1 | KIDNEY, 65 M |
| CONNTUT05 | 1 | SKULL TUMOR, EPENDYOMA, 34 F |
| BRSTNOT16 | 1 | BREAST, PAPILLOMATOSIS, 59 F |
| BONRFET01 | 1 | RIB, FETAL M |

FIGURE 9

| LIBRARY | ABUN | LIBRARY DESCRIPTION |
|---|---|---|
| LUNGNON03 | 2 | LUNG, 58, NORM |
| COLNTUT03 | 2 | COLON TUMOR, 62 M, MATCH TO COLNNOT16 |
| THYRNOT10 | 1 | THYROID, LYMPHOCYTIC THYROIDITIS, 30 F |
| THP1AZT01 | 1 | THP-1 PROMONOCYTE CELL LINE, TREATED AZ |
| STOMFET02 | 1 | STOMACH, FETAL M |
| SMCCNOT02 | 1 | SMOOTH MUSCLE CELLS, CORONARY ARTERY, 3 M |
| SINJNOT02 | 1 | SMALL INTESTINE, JEJUNUM, 8 F |
| SCORNON02 | 1 | SPINAL CORD, 71 M, NORM |
| PROSTUT16 | 1 | PROSTATE TUMOR, ADENOCARCINOMA, 55 M, |
| PROSTUT05 | 1 | PROSTATE TUMOR, 69 M, MATCH TO PROSNOT07 |
| PROSBPT02 | 1 | PROSTATE, HYPERPLASIA, 65 M |
| PENCNOT05 | 1 | PENIS, LEFT CORPUS CAVERNOSUM, M |
| OVARTUT03 | 1 | OVARIAN TUMOR, CARCINOMA, 52 F |
| LVENNOT03 | 1 | HEART, LEFT VENTRICLE, 31 M |
| LUNGTUT07 | 1 | LUNG TUMOR, 50 M |
| LUNGNOT03 | 1 | LUNG, 79 M, MATCH TO LUNGTUT02 |
| DRGLNOT01 | 1 | GANGLION, DORSAL ROOT, THORACIC/LUMBAR, 3 |
| CONNTUT01 | 1 | SKULL TUMOR, CHONDROID CHORDOMA, 30 F |
| BRSTTUT15 | 1 | BREAST TUMOR, ADENOCARCINOMA, 46 F |
| BRSTTUT03 | 1 | BREAST TUMOR, 58 F, MATCH TO BRSTNOT05 |
| BRONNOT01 | 1 | BRONCHUS, 15 M |

FIGURE 10

| LIBRARY | ABUN | LIBRARY DESCRIPTION |
|---|---|---|
| SMCCNOT01 | 2 | SMOOTH MUSCLE CELLS, CORONARY ARTERY, 3 M |
| SMCCNON03 | 2 | SMOOTH MUSCLE CELLS, CORONARY ARTERY, 3M, NORM |
| BEPINOT01 | 2 | BRONCHIAL EPITHELIUM, PRIMARY CELL LINE, |
| THYRTUT03 | 1 | THYROID TUMOR, BENIGN, 17 M |
| SKINNOT04 | 1 | BREAST SKIN, 70 F |
| PROSNOT16 | 1 | PROSTATE, 68 M |
| PROSNOT14 | 1 | PROSTATE, 60 M, MATCH TO PROSTUT08 |
| OVARNOT10 | 1 | OVARY, 52 F |
| LUNGNOT10 | 1 | LUNG, FETAL M |
| LUNGNOT09 | 1 | LUNG, FETAL M |
| KERANOT02 | 1 | KERATINOCYTES, PRIMARY CELL LINE, 30 F |
| HNT3AZT01 | 1 | HNT2 CELL LINE, TERATOCARCINOMA, TREATED |
| HNT2AZS07 | 1 | HNT2 CELL LINE, TERATOCARCINOMA, TREATED |
| CONNTUT01 | 1 | SKULL TUMOR, CHONDROID CHORDOMA, 30 F |
| BRSTNOT07 | 1 | BREAST, 43 F |
| BRAITUT22 | 1 | BRAIN TUMOR, FRONTAL PARIETAL, 76 F |

SEQUENCE LISTING

```
(1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 111 amino acids
        (B) TYPE: amino acid
        (C) STRANDEDNESS: single
        (D) TOPOLOGY: linear (vii) IMMEDIATE SOURCE:
        (A) LIBRARY: PROSTUT05
        (B) CLONE: 1793721

(xi) SEQUENCE DESCRIPTION: SEQ ID NO: 1:

Met Ala Asp Trp Ala Arg Ala Gln Ser Pro Gly Ala Val Glu Glu Ile
1               5                   10                  15
```

```
Leu Asp Arg Glu Asn Lys Arg Met Ala Asp Ser Leu Ala Ser Lys Val
            20                  25                  30

Thr Arg Leu Lys Ser Leu Ala Leu Asp Ile Asp Arg Asp Ala Glu Asp
        35                  40                  45

Gln Asn Arg Tyr Leu Asp Gly Met Asp Ser Asp Phe Thr Ser Met Thr
    50                  55                  60

Ser Leu Leu Thr Gly Ser Val Lys Arg Phe Ser Thr Met Ala Arg Ser
65                  70                  75                  80

Gly Gln Asp Asn Arg Lys Leu Leu Cys Gly Met Ala Val Gly Leu Ile
                85                  90                  95

Val Ala Phe Phe Ile Leu Ser Tyr Phe Leu Ser Arg Ala Arg Thr
            100                 105                 110

(2) INFORMATION FOR SEQ ID NO: 2:

(i) SEQUENCE CHARACTERISTICS:
        (A) LENGTH: 524 base pairs
        (B) TYPE: nucleic acid
        (C) STRANDEDNESS: single
        (D) TOPOLOGY: linear (vii) IMMEDIATE SOURCE:
        (A) LIBRARY: PROSTUT05
        (B) CLONE: 1793721

(xi) SEQUENCE DESCRIPTION: SEQ ID NO: 2:

GGCCACGTCT GAGGCGGCTG TGGCCGCGTG CGGTGTCCGC GTCGAGGAGC CGGGGCAGGG      60

CACGATGGCG GACTGGGCTC GGGCTCAGAG CCCGGGCGCT GTGGAAGAGA TTCTAGACCG     120

GGAGAACAAG CGAATGGCTG ACAGCCTGGC CTCCAAAGTC ACCAGGCTCA AATCGCTCGC     180

CCTGGACATC GATAGGGATG CAGAGGATCA GAACCGGTAC CTGGATGGCA TGGACTCGGA     240

TTTCACAAGC ATGACCAGCC TGCTTACAGG GAGCGTGAAG CGCTTTTCCA CAATGGCAAG     300

GTCCGGACAA GACAACCGGA AGCTTCTATG TGGCATGGCC GTGGGTCTAA TTGTGGCCTT     360

CTTCATCCTC TCCTACTTCT TGTCCAGGGC AAGGACGTGA GCCAGTGGGA GCTGGTGTCT     420

GTGGGTGCCA AGGGCAGCCA GGGTCTTCCC TGCCTGGTGT TTTGGGCTCC AGAGGACTTA     480

CCTACAAAAT ACTCCTTTGC AATTATAAAA AAAAAAAAA AAAA                     524

(2) INFORMATION FOR SEQ ID NO: 3:

(i) SEQUENCE CHARACTERISTICS:
        (A) LENGTH: 307 amino acids
        (B) TYPE: amino acid
        (C) STRANDEDNESS: single
        (D) TOPOLOGY: linear (vii) IMMEDIATE SOURCE:
        (A) LIBRARY: LUNGTUT07
        (B) CLONE: 2607662

(xi) SEQUENCE DESCRIPTION: SEQ ID NO: 3:

Met Ser Met Ile Leu Ser Ala Ser Val Ile Arg Val Arg Asp Gly Leu
1               5                   10                  15

Pro Leu Ser Ala Ser Thr Asp Tyr Glu Gln Ser Thr Gly Met Gln Glu
            20                  25                  30

Cys Arg Lys Tyr Phe Lys Met Leu Ser Arg Lys Leu Ala Gln Leu Pro
        35                  40                  45

Asp Arg Cys Thr Leu Lys Thr Gly His Tyr Asn Ile Asn Phe Ile Ser
    50                  55                  60
```

```
Ser Leu Gly Val Ser Tyr Met Met Leu Cys Thr Glu Asn Tyr Pro Asn
 65                  70                  75                  80

Val Leu Ala Phe Ser Phe Leu Asp Glu Leu Gln Lys Glu Phe Ile Thr
             85                  90                  95

Thr Tyr Asn Met Met Lys Thr Asn Thr Ala Val Arg Pro Tyr Cys Phe
            100                 105                 110

Ile Glu Phe Asp Asn Phe Ile Gln Arg Thr Lys Gln Arg Tyr Asn Asn
            115                 120                 125

Pro Arg Ser Leu Ser Thr Lys Ile Asn Leu Ser Asp Met Gln Thr Glu
        130                 135                 140

Ile Lys Leu Arg Pro Pro Tyr Gln Ile Ser Met Cys Glu Leu Gly Ser
145                 150                 155                 160

Ala Asn Gly Val Thr Ser Ala Phe Ser Val Asp Cys Lys Gly Ala Gly
                165                 170                 175

Lys Ile Ser Ser Ala His Gln Arg Leu Glu Pro Ala Thr Leu Ser Gly
            180                 185                 190

Ile Val Gly Phe Ile Leu Ser Leu Leu Cys Gly Ala Leu Asn Leu Ile
            195                 200                 205

Arg Gly Phe His Ala Ile Glu Ser Leu Leu Gln Ser Asp Gly Asp Asp
        210                 215                 220

Phe Asn Tyr Ile Ile Ala Phe Phe Leu Gly Thr Ala Ala Cys Leu Tyr
225                 230                 235                 240

Gln Cys Tyr Leu Leu Val Tyr Tyr Thr Gly Trp Arg Asn Val Lys Ser
                245                 250                 255

Phe Leu Thr Phe Gly Leu Ile Cys Leu Cys Asn Met Tyr Leu Tyr Glu
            260                 265                 270

Leu Arg Asn Leu Trp Gln Leu Phe Phe His Val Thr Val Gly Ala Phe
        275                 280                 285

Val Thr Leu Gln Ile Trp Leu Arg Gln Ala Gln Gly Lys Ala Pro Asp
        290                 295                 300

Tyr Asp Val
305

(2) INFORMATION FOR SEQ ID NO: 4:

(i) SEQUENCE CHARACTERISTICS:
        (A) LENGTH: 1423 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT07
        (B) CLONE: 2607662

(xi) SEQUENCE DESCRIPTION: SEQ ID NO: 4:

CGGAATTCGG CTCGAGGTCT CGACAGGTTT TCTCTGTTGG TTGAAATGTC TATGATTTTA      60

TCTGCCTCAG TCATTCGTGT CAGAGATGGA CTGCCACTTT CTGCTTCTAC TGATTATGAA     120

CAAAGCACAG GAATGCAGGA GTGCAGAAAG TATTTTAAAA TGCTTTCGAG GAAACTTGCT     180

CAACTTCCTG ATAGATGTAC ACTGAAAACT GGACATTATA ACATTAATTT TATTAGCTCT     240

CTGGGAGTGA GCTACATGAT GTTGTGCACT GAAAATTACC CAAATGTTCT CGCCTTCTCT     300

TTCCTGGATG AGCTTCAGAA GGAGTTCATT ACTACTTATA ACATGATGAA GACAAATACT     360

GCTGTCAGAC CATACTGTTT CATTGAATTT GATAACTTCA TTCAGAGGAC CAAGCAGCGA     420

TATAATAATC CCAGGTCTCT TTCAACAAAG ATAAATCTTT CTGACATGCA GACGGAAATC     480
```

-continued

```
AAGCTGAGGC CTCCTTATCA AATTTCCATG TGCGAACTGG GGTCAGCCAA TGGAGTCACA      540

TCAGCATTTT CTGTTGACTG TAAAGGTGCT GGTAAGATTT CTTCTGCTCA CCAGCGACTG      600

GAACCAGCAA CTCTGTCAGG GATTGTAGGA TTTATCCTTA GTCTTTTATG TGGAGCTCTG      660

AATTTAATTC GAGGCTTTCA TGCTATAGAA AGTCTCCTGC AGAGTGATGG TGATGATTTT      720

AATTACATCA TTGCATTTTT CCTTGGAACA GCAGCCTGCC TTTACCAGTG TTATTTACTT      780

GTCTACTACA CCGGCTGGCG GAATGTCAAA TCTTTTTTGA CTTTTGGCTT AATCTGTCTA      840

TGCAACATGT ATCTCTATGA ACTGCGCAAC CTCTGGCAGC TTTTCTTTCA TGTGACTGTG      900

GGAGCATTTG TTACACTACA GATCTGGCTA AGGCAAGCCC AGGGCAAGGC TCCCGATTAT      960

GATGTCTGAC ACCATCCTTC AGATCTATTG CCTTGGCTTC AGGGGATAA GGAGGGAACA     1020

TATCATAACT GCACTGTGAT GAAGAAGCTG TTCCCCACAG AGGAGAAGCT CTGCTTTCTT     1080

TCTCTCCAAC TTTCCTTTTT TAAAATCAGC ATGATGTGCC TGTGAGCATG AAGAGTCCT     1140

CTCAGAAGAA TGTTGGCCAT GAGACTATCA TTCAGAGGAG GAGGGATTT CTCTCTTCAA     1200

GGCCATAACA GTGAAGAAC AGTCATATGC CATTGGAAGT CTTGGCCAGC AGTCCTGAAT     1260

CCTTCCTGAA GAGTTCAGAA AATAGATGTG GTATTGCTCT GAGGACCAGG CAGGAGGAAC     1320

TCTACAACCT GAGTTTGCCT TTGTGAGGCA TTAGTATAGA CCAAATAAAA AGCTGCAGAA     1380

ATTGGAAAGT TTATGTTTTA AATAAATGAC TGTGATAAAT ATC                        1423
```

(2) INFORMATION FOR SEQ ID NO: 5:

(i) SEQUENCE CHARACTERISTICS:
        (A) LENGTH: 210 amino acids
        (B) TYPE: amino acid
        (C) STRANDEDNESS: single
        (D) TOPOLOGY: linear (vii) IMMEDIATE SOURCE:
        (A) LIBRARY: KERANOT02
        (B) CLONE: 2620104

(xi) SEQUENCE DESCRIPTION: SEQ ID NO: 5:

```
Met Thr Ala Ala Gln Ala Ala Gly Glu Glu Ala Pro Pro Gly Val Arg
 1               5                  10                  15

Ser Val Lys Val Val Leu Val Gly Asp Gly Gly Cys Gly Lys Thr Ser
            20                  25                  30

Leu Leu Met Val Phe Ala Asp Gly Ala Phe Pro Glu Ser Tyr Thr Pro
        35                  40                  45

Thr Val Phe Glu Arg Tyr Met Val Asn Leu Gln Val Lys Gly Lys Pro
    50                  55                  60

Val His Leu His Ile Trp Asp Thr Ala Gly Gln Asp Asp Tyr Asp Arg
65                  70                  75                  80

Leu Arg Pro Leu Phe Tyr Pro Asp Ala Ser Val Leu Leu Cys Phe
                85                  90                  95

Asp Val Thr Ser Pro Asn Ser Phe Asp Asn Ile Phe Asn Arg Trp Tyr
            100                 105                 110

Pro Glu Val Asn His Phe Cys Lys Lys Val Pro Ile Ile Val Val Gly
        115                 120                 125

Cys Lys Thr Asp Leu Arg Lys Asp Lys Ser Leu Val Asn Lys Leu Arg
    130                 135                 140

Arg Asn Gly Leu Glu Pro Val Thr Tyr His Arg Gly Gln Glu Met Ala
145                 150                 155                 160

Arg Ser Val Gly Ala Val Ala Tyr Leu Glu Cys Ser Ala Arg Leu His
                165                 170                 175
```

Asp Asn Val His Ala Val Phe Gln Glu Ala Ala Glu Val Ala Leu Ser
            180                 185                 190

Ser Arg Gly Arg Asn Phe Trp Arg Arg Ile Thr Gln Gly Phe Cys Val
        195                 200                 205

Val Thr
    210

(2) INFORMATION FOR SEQ ID NO: 6:

(i) SEQUENCE CHARACTERISTICS:
       (A) LENGTH: 1098 base pairs
       (B) TYPE: nucleic acid
       (C) STRANDEDNESS: single
       (D) TOPOLOGY: linear (vii) IMMEDIATE SOURCE:
       (A) LIBRARY: KERANOT02
       (B) CLONE: 2620104

(xi) SEQUENCE DESCRIPTION: SEQ ID NO: 6:

| | | | | | |
|---|---|---|---|---|---|
| GGTCTCTGCG | CCGCAGCCGC | CCGCCCGCCC | GCTCAGCGCC | CGGCCCCGGG | ATGACGGCGG | 60 |
| CCCAGGCCGC | GGGTGAGGAG | GCGCCACCAG | GCGTGCGGTC | CGTCAAGGTG | GTCCTGGTGG | 120 |
| GCGACGGCGG | CTGCGGGAAG | ACGTCGCTGC | TGATGGTCTT | CGCCGATGGG | GCCTTCCCCG | 180 |
| AGAGCTACAC | CCCCACGGTG | TTTGAGCGGT | ACATGGTCAA | CCTGCAAGTG | AAAGGCAAAC | 240 |
| CTGTGCACCT | CCACATCTGG | GACACAGCAG | GGCAAGATGA | CTATGACCGC | CTGCGGCCCC | 300 |
| TGTTCTACCC | TGACGCCAGC | GTCCTGCTGC | TTTGCTTCGA | TGTCACCAGC | CCGAACAGCT | 360 |
| TTGACAACAT | CTTTAACCGG | TGGTACCCAG | AAGTGAATCA | TTTCTGCAAG | AAGGTACCCA | 420 |
| TCATCGTCGT | GGGCTGCAAG | ACTGACCTGC | GCAAGGACAA | ATCACTGGTG | AACAAGCTCC | 480 |
| GAAGAAACGG | ATTGGAGCCT | GTGACCTACC | ACAGGGGCCA | GGAGATGGCG | AGGTCCGTGG | 540 |
| GCGCGGTGGC | CTACCTCGAG | TGCTCGGCTC | GGCTCCATGA | CAACGTCCAC | GCCGTCTTCC | 600 |
| AGGAGGCCGC | CGAGGTGGCC | CTCAGCAGCC | GCGGTCGCAA | CTTCTGGCGG | CGGATTACCC | 660 |
| AGGGCTTTTG | CGTGGTGACC | TGAGCGGCTC | GGGGCGTCCC | AGCGACGCGG | GAAGGGGCAG | 720 |
| GGCGCTGACC | TGCTGCTGAG | CTGGCTGGGC | TGGACCCGGT | CCCTAGGCTG | TGACCGCCGA | 780 |
| ACTCCACTGC | AACAGACGGG | CGCCACCAAA | GCCAGGCCCT | GAGGCCTGGG | AGTCCTGGAC | 840 |
| TGAGAAAGGG | GGTTCCTGGG | CCCACCTGCT | CTGTGTAGGG | CTCGTCCTGC | GGTGCCCGAG | 900 |
| AATCACTCGC | TAACCCCTAT | GCCCGGTCCC | GGACCGACAT | CCTGGAGCCG | CCTGTGCAGC | 960 |
| CTGATGCCCC | CTCGTGGCTG | CTCCCAGGGC | TGCACCTGCC | AGGACCTAAT | GTTCTTAGGT | 1020 |
| CCCTCTGGCC | AGAACCCACA | CCCGGCCCCT | TCCCACCTGT | CATACTGGTA | ACTGTAACAA | 1080 |
| GAAAAACGAC | ATCACTTA | | | | | 1098 |

(2) INFORMATION FOR SEQ ID NO: 7:

(i) SEQUENCE CHARACTERISTICS:
       (A) LENGTH: 111 amino acids
       (B) TYPE: amino acid
       (C) STRANDEDNESS: single
       (D) TOPOLOGY: linear (vii) IMMEDIATE SOURCE:
       (A) LIBRARY: GenBank
       (B) CLONE: 2316080

(xi) SEQUENCE DESCRIPTION: SEQ ID NO: 7:

-continued

```
Met Ala Asp Trp Thr Arg Ala Gln Ser Ser Gly Ala Val Glu Asp Ile
1               5                   10                  15

Leu Asp Arg Glu Asn Lys Arg Met Ala Asp Ser Leu Ala Ser Lys Val
                20                  25                  30

Thr Arg Leu Lys Ser Leu Ala Leu Asp Ile Asp Arg Asp Thr Glu Asp
            35                  40                  45

Gln Asn Arg Tyr Leu Asp Gly Met Asp Ser Asp Phe Thr Ser Val Thr
    50                  55                  60

Gly Leu Leu Thr Gly Ser Val Lys Arg Phe Ser Thr Met Ala Arg Ser
65                  70                  75                  80

Gly Arg Asp Asn Arg Lys Leu Leu Cys Gly Met Ala Val Val Leu Ile
                85                  90                  95

Val Ala Phe Phe Ile Leu Ser Tyr Leu Leu Ser Arg Thr Arg Thr
                100                 105                 110
```

(2) INFORMATION FOR SEQ ID NO: 8:

(i) SEQUENCE CHARACTERISTICS:
        (A) LENGTH: 118 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 2253428

(xi) SEQUENCE DESCRIPTION: SEQ ID NO: 8:

```
Met Arg Arg Ala Gly Leu Gly Asp Gly Ala Pro Pro Gly Ser Tyr Gly
1               5                   10                  15

Asn Tyr Gly Tyr Ala Asn Thr Gly Tyr Asn Ala Cys Glu Glu Glu Asn
                20                  25                  30

Asp Arg Leu Thr Glu Ser Leu Arg Ser Lys Val Thr Ala Ile Lys Ser
            35                  40                  45

Leu Ser Ile Glu Ile Gly His Glu Val Lys Asn Gln Asn Lys Leu Leu
    50                  55                  60

Ala Glu Met Asp Ser Gln Phe Asp Ser Thr Thr Gly Phe Leu Gly Lys
65                  70                  75                  80

Thr Met Gly Arg Leu Lys Ile Leu Ser Arg Gly Ser Gln Thr Lys Leu
                85                  90                  95

Leu Cys Tyr Met Met Leu Phe Ser Leu Phe Val Phe Val Ile Tyr
                100                 105                 110

Trp Ile Ile Lys Leu Arg
        115
```

(2) INFORMATION FOR SEQ ID NO: 9:

(i) SEQUENCE CHARACTERISTICS:
        (A) LENGTH: 254 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1223894

(xi) SEQUENCE DESCRIPTION: SEQ ID NO: 9:

```
Met Ser Met Ile Leu Ser Ala Ser Val Val Arg Val Arg Asp Gly Leu
1               5                   10                  15
```

-continued

```
Pro Leu Ser Ala Ser Thr Asp Cys Glu Gln Ser Ala Gly Val Gln Glu
             20                  25                  30

Cys Arg Lys Tyr Phe Lys Met Leu Ser Arg Lys Leu Ala Gln Phe Pro
         35                  40                  45

Asp Arg Cys Thr Leu Lys Thr Gly Arg His Asn Ile Asn Phe Ile Ser
     50                  55                  60

Ser Leu Gly Val Ser Tyr Met Met Leu Cys Thr Glu Asn Tyr Pro Asn
 65                  70                  75                  80

Val Leu Ala Phe Ser Phe Leu Asp Glu Leu Gln Lys Glu Phe Ile Thr
                 85                  90                  95

Thr Tyr Asn Met Met Lys Thr Asn Thr Ala Val Arg Pro Tyr Cys Phe
                100                 105                 110

Ile Glu Phe Asp Asn Phe Ile Gln Arg Thr Lys Gln Arg Tyr Asn Asn
            115                 120                 125

Pro Arg Ser Leu Ser Thr Lys Ile Asn Leu Ser Asp Met Gln Met Glu
        130                 135                 140

Ile Lys Leu Arg Pro Pro Tyr Gln Ile Pro Met Cys Glu Leu Gly Ser
145                 150                 155                 160

Ala Asn Gly Val Thr Ser Ala Phe Ser Val Asp Cys Lys Gly Ala Gly
                165                 170                 175

Lys Ile Ser Ser Ala His Gln Arg Leu Glu Pro Ala Thr Leu Ser Gly
            180                 185                 190

Ile Val Ala Phe Ile Leu Ser Leu Leu Cys Gly Ala Leu Asn Leu Ile
        195                 200                 205

Arg Gly Phe His Ala Ile Glu Ser Leu Leu Gln Ser Asp Gly Glu Asp
    210                 215                 220

Phe Ser Tyr Met Ile Ala Phe Phe Leu Gly Thr Ala Ala Cys Leu Tyr
225                 230                 235                 240

Gln Met Ile Cys Leu Cys Leu Gln Gly Arg Lys Glu Arg Thr
                245                 250
```

(2) INFORMATION FOR SEQ ID NO: 10:

(i) SEQUENCE CHARACTERISTICS:
        (A) LENGTH: 210 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1702943

(xi) SEQUENCE DESCRIPTION: SEQ ID NO: 10:

```
Met Asn Ala Ser Gln Val Ala Gly Glu Glu Ala Pro Gln Ser Gly His
  1               5                  10                  15

Ser Val Lys Val Val Leu Val Gly Asp Gly Gly Cys Gly Lys Thr Ser
             20                  25                  30

Leu Met Met Val Phe Ala Lys Gly Ala Phe Pro Glu Ser Tyr Ser Pro
         35                  40                  45

Thr Val Phe Glu Arg Tyr Asn Ala Thr Leu Gln Met Lys Gly Lys Pro
     50                  55                  60

Val His Leu Gln Ile Trp Asp Thr Ala Gly Gln Asp Asp Tyr Asp Arg
 65                  70                  75                  80

Leu Arg Pro Leu Phe Tyr Pro Asp Ala Asn Val Leu Leu Leu Cys Phe
                 85                  90                  95
```

```
Asp Val Thr Asn Pro Asn Ser Phe Asp Asn Val Ser Asn Arg Trp Tyr
            100                 105                 110

Pro Glu Val Thr His Phe Cys Lys Gly Val Pro Ile Ile Val Val Gly
            115                 120                 125

Cys Lys Ile Asp Leu Arg Lys Asp Lys Val Leu Val Asn Asn Leu Arg
            130                 135                 140

Lys Lys Arg Leu Glu Pro Val Thr Tyr His Arg Gly His Asp Met Ala
145                 150                 155                 160

Arg Ser Val Gly Ala Val Ala Tyr Leu Glu Cys Ser Ala Arg Leu His
                165                 170                 175

Asp Asn Val Glu Ala Val Phe Gln Glu Ala Glu Val Ala Leu Ser
                180                 185                 190

Ser Arg Arg His Asn Phe Trp Arg Arg Ile Thr Gln Asn Cys Cys Leu
                195                 200                 205

Ala Thr
    210
```

(2) INFORMATION FOR SEQ ID NO: 11:

(i) SEQUENCE CHARACTERISTICS:
        (A) LENGTH: 202 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1064856

(xi) SEQUENCE DESCRIPTION: SEQ ID NO: 11:

```
Met Ala Thr Glu Leu Arg Arg Lys Leu Val Ile Val Gly Asp Gly Ala
1               5                   10                  15

Cys Gly Lys Thr Cys Leu Leu Ile Val Phe Ser Lys Gly Thr Phe Pro
            20                  25                  30

Glu Val Tyr Val Pro Thr Val Phe Glu Asn Tyr Val Ala Asp Val Glu
            35                  40                  45

Val Asp Gly Arg His Val Glu Leu Ala Leu Trp Asp Thr Ala Gly Gln
50                  55                  60

Glu Asp Tyr Asp Arg Leu Arg Pro Leu Ser Tyr Pro Asp Ser His Val
65                  70                  75                  80

Ile Leu Ile Cys Phe Ala Val Asp Ser Pro Asp Ser Leu Asp Asn Val
                85                  90                  95

Gln Glu Lys Trp Ile Ser Glu Val Leu His Phe Cys Ser Ser Leu Pro
            100                 105                 110

Ile Leu Leu Val Ala Cys Lys Ala Asp Leu Arg Asn Asp Pro Lys Ile
            115                 120                 125

Ile Glu Glu Leu Ser Lys Thr Asn Gln His Pro Val Thr Thr Glu Glu
            130                 135                 140

Gly Gln Ala Val Ala Gln Lys Ile Gly Ala Tyr Lys Tyr Leu Glu Cys
145                 150                 155                 160

Ser Ala Lys Thr Asn Glu Gly Val Arg Glu Val Phe Glu Ser Ala Thr
                165                 170                 175

Arg Ala Ala Met Leu Lys His Lys Pro Lys Val Lys Pro Ser Ser Gly
                180                 185                 190

Thr Lys Lys Lys Lys Arg Cys Ile Leu Leu
                195                 200
```

VESICLE TRANSPORT ASSOCIATED PROTEINS

This application is a divisional application of U.S. application Ser. No. 09/193,510, filed Nov. 17, 1998, now U.S. Pat. No. 5,981,226 which is a division of U.S. application Ser. No. 08/948,616 filed Oct. 10, 1997, now U.S. Pat. No. 5,840,539.

FIELD OF THE INVENTION

This invention relates to nucleic acid and amino acid sequences of three vesicle transport associated proteins and to the use of these sequences in the diagnosis, prevention, and treatment of cancer, and immune, reproductive, and developmental disorders.

BACKGROUND OF THE INVENTION

Vesicle transport is the general process in eukaryotic cells by which proteins synthesized in the endoplasmic reticulum (ER) are transported via the Golgi network to the various compartments in the cell where they will function. Other proteins are transported to the cell surface by this process where they may be secreted (exocytosis). Such proteins include membrane bound receptors or other membrane proteins, neurotransmitters, hormones, and digestive enzymes. The transport process uses a series of transport vesicles that shuttle a protein from one membrane-bound compartment (donor compartment) to another (acceptor compartment) until the protein reaches its proper destination (Rothman, J. E. and Wieland, F. T. (1996) Science 272:227–34).

The process begins with the budding of a vesicle out of the donor membrane. The vesicle contains the protein to be transported and is surrounded by a protective coat made up of protein subunits recruited from the cytosol. The initial budding process and coating processes are controlled by cytosolic GTP-binding proteins (GTPB). When GTP binds and activates the GTPB, the GTP-GTPB complex binds to the donor membrane and initiates the vesicle assembly process. The coated vesicle containing the GTP-GTPB complex detaches from the donor compartment and is transported through the cytosol. During the transport process, the GTP is hydrolyzed to GDP, and the inactivated GTPB dissociates from the transport vesicle and is recycled. At this point, the protective coat of the vesicle becomes unstable and dissociates from the enclosed vesicle. The uncoated vesicle is recognized by its acceptor compartment through exposed surface identifiers (v-SNAREs) which bind with corresponding molecules on the acceptor compartment membrane (t-SNAREs). The transport process ends when the vesicle fuses with the target membrane.

Many of the proteins involved in synaptic vesicle transport have been identified and the biochemical interactions between them have been characterized. Interestingly, many of these proteins are homologous to yeast proteins involved in yeast secretory pathways. For example, BET1, BOS1, and SEC22 form a set of interacting yeast genes required in endoplasmic reticulum (ER) to Golgi protein transport (Newman, A. P. et al. (1992) EMBO Journal 11: 3609–17). Each of these genes encodes a small integral membrane protein with hydrophilic, cytoplasmic N-terminal and central regions, and a C-terminal hydrophobic transmembrane anchor. Mammalian counterparts of yeast bet1 and sec22 have been identified (Hay, J. C. et al. (1996) J. Biol. Chem. 271: 5671–79). Both proteins are widely expressed in mammalian tissues, as would be expected of proteins involved in fundamental membrane trafficking reactions. Mammalian bet1 and sec22 are localized to the ER membrane and the Golgi membrane, respectively, indicating that they may participate in vesicle transport in opposite directions between the ER and the Golgi apparatus (Hay et al. supra).

GTP-binding/GTPase proteins are likewise essential in both yeast and mammalian secretory pathways. At least four genes encoding GTPB's have been shown to be involved in transport between ER and the plasma membrane. These include SEC4, YPT1, SAR1, and ARF1 (Dascher, C. et al. (1991) Mol. Cell. Biol. 11:872–85). Yeast sec4 GTPB, essential for late stages of vesicle secretion, is homologous to mammalian Ra3a GTPase. The Rho proteins are another small family of GTPBs found in both yeast and mammals (Nakano, K. and Issei, M. (1995) Gene 155: 119–22). Rho proteins regulate the actin cytoskeleton during cell division and control signal transduction by linking receptors of growth factors to actin polymerization. RhoD is a member of the mammalian Rho family that provides a link between membrane trafficking and cytoskeleton regulation. RhoD causes rearrangements of the actin cytoskeleton and cell surface, and governs endosome motility and distribution (Murphy, C. et al. (1996) Nature 384: 427–32).

GTP-binding proteins share several amino acid sequence motifs, termed motifs I–IV. Motif I has the signature, GXXXXGK. The lysine residue is essential in interacting with the β- and γ-phosphates of GTP. Motif II, III, and IV are highly conserved, with DTAGQ, NKXD, EXSAK/L as their respective signatures. These motifs regulate the binding of γ-phosphate, GTP, and the guanine base of GTP, respectively. In addition, Rho proteins have a Cys-aliphatic residue-aliphatic residue-X (CAAX) box for the binding of a prenyl group and either a palmitoylation site or a basic amino acid-rich region, suggesting their role in membrane-associated functions.

The discovery of new vesicle transport associated proteins and the polynucleotides encoding it satisfies a need in the art by providing new compositions which are useful in the diagnosis, prevention and treatment of cancer, and immune, reproductive, and developmental disorders.

SUMMARY OF THE INVENTION

The invention features three substantially purified polypeptides, vesicle transport associated proteins VTAP-1, VTAP-2, and VTAP-3 (referred to collectively as VTAP), having the amino acid sequences shown in SEQ ID NO:1, SEQ ID NO:3, and SEQ ID NO:5, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequences SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments of variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding VTAP-1 under conditions suitable for the expression of the polypeptide; and b) recovering the polypeptide from the host cell culture.

The invention also provides a pharmaceutical composition comprising a substantially purified VTAP-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing cancer comprising administering to a subject in need of such treatment an effective amount of a purified antagonist of VTAP-1.

The invention also provides a method for treating or preventing a reproductive disorder comprising administering to a subject in need of such treatment an effective amount of a purified antagonist of VTAP-1.

The invention also provides a method for detecting a polynucleotide which encodes VTAP-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding VTAP-1 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3, or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4 or variants thereof. In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3 or a fragment thereof, the method comprising the steps of: a) culturing the host cell containing an expression vector containing at least a fragment of the polynucleotide sequence encoding VTAP-2 under conditions suitable for the expression of the polypeptide; and b) recovering the polypeptide from the host cell culture.

The invention also provides a pharmaceutical composition comprising a substantially purified VTAP-2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for treating or preventing cancer comprising administering to a subject in need of such treatment an effective amount of a purified antagonist of VTAP-2.

The invention also provides a method for treating or preventing an immune disorder comprising administering to a subject in need of such treatment an effective amount of a purified antagonist of VTAP-2.

The invention also provides a method for detecting a polynucleotide which encodes VTAP-2 in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding VTAP-2 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:5 or fragments thereof and a composition comprising said polynucleotide sequence. The invention also provides a polynucleotide sequence which hybridizes under stringent conditions to the polynucleotide sequence encoding the amino acid sequence SEQ ID NO:5, or fragments of said polynucleotide sequence. The invention further provides a polynucleotide sequence comprising the complement of the polynucleotide sequence encoding the amino acid sequence of SEQ ID NO:5, or fragments or variants of said polynucleotide sequence.

The invention also provides an isolated and purified sequence comprising SEQ ID NO:6 of variants thereof. In addition, the invention provides a polynucleotide sequence which hybridizes under stringent conditions to the polynucleotide sequence of SEQ ID NO:6. The invention also provides a polynucleotide sequence comprising the complement of SEQ ID NO:6, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:5 or a fragment thereof, the method comprising the steps of: a) culturing the host cell containing an expression vector containing at least a fragment of the polynucleotide sequence encoding VTAP-3 under conditions suitable for the expression of the polypeptide; and b) recovering the polypeptide from the host cell culture.

The invention also provides a pharmaceutical composition comprising a substantially purified VTAP-3 having the amino acid sequence of SEQ ID NO:5 in conjunction with a suitable pharmaceutical carrier.

The invention also provides a purified antagonist of the polypeptide of SEQ ID NO:5. In one aspect the invention provides a purified antibody which binds to a polypeptide comprising the amino acid sequence of SEQ ID NO:5.

Still further, the invention provides a purified agonist of the polypeptide of SEQ ID NO:5.

The invention also provides a method for treating or preventing a developmental disorder comprising administering to a subject in need of such treatment an effective amount of a pharmaceutical composition comprising purified VTAP-3.

The invention also provides a method for treating or preventing cancer comprising administering to a subject in need of such treatment an effective amount of a purified antagonist of VTAP-3.

The invention also provides a method for detecting a polynucleotide which encodes VTAP-3 in a biological sample comprising the steps of: a) hybridizing the complement of the polynucleotide sequence which encodes SEQ ID NO:5 to nucleic acid material of a biological sample, thereby forming a hybridization complex; and b) detecting the hybridization complex, wherein the presence of the complex correlates with the presence of a polynucleotide encoding VTAP-3 in the biological sample. In one aspect the nucleic acid material of the biological sample is amplified by the polymerase chain reaction prior to hybridization.

BRIEF DESCRIPTION OF THE FIGURES

FIGS. 1A and 1B show the amino acid sequence (SEQ ID NO:1) and nucleic acid sequence (SEQ ID NO:2) of VTAP-1. The alignment was produced using MACDNASIS PRO™ software (Hitachi Software Engineering Co. Ltd. San Bruno, Calif.).

FIGS. 2A, 2B, 2C, and 2D show the amino acid sequence (SEQ ID NO:3) and nucleic acid sequence (SEQ ID NO:4) of VTAP-2. The alignment was produced using MACDNASIS PRO™ software.

FIGS. 3A, 3B, and 3C show the amino acid sequence (SEQ ID NO:5) and nucleic acid sequence (SEQ ID NO:6) of VTAP-3. The alignment was produced using MACDNASIS PRO™ software.

FIG. 4 shows the amino acid sequence alignments among VTAP-1 (1793721; SEQ ID NO:1), the mouse-Golgi SNARE protein, GS 15 (GI 2316080; SEQ ID NO:7) and the mouse homolog of yeast BET1, mBET1 (GI 2253428; SEQ ID NO:8), produced using the multisequence alignment program of DNASTAR™ software (DNASTAR Inc, Madison Wis.).

FIG. 5 shows the amino acid sequence alignments among VTAP-2 (2607662; SEQ ID NO:3), and rat SEC22 (GI 1223894; SEQ ID NO:9), produced using the multisequence alignment program of DNASTAR™ software.

FIG. 6 shows the amino acid sequence alignments among VTAP-3 (2620104; SEQ ID NO:5), mouse RhoD protein (GI 1702943; SEQ ID NO:10) and yeast Rho1 (GI 1064856; SEQ ID NO:11), produced using the multisequence alignment program of DNASTAR™ software.

FIG. 9 shows the northern analysis for VTAP-1, produced electronically using LIFESEQ™ database (Incyte Pharmaceuticals, Inc., Palo Alto, Calif.).

FIG. 10 shows the northern analysis for VTAP-2, produced electronically using LIFESEQ™ database.

FIG. 11 shows the northern analysis for VTAP-3, produced electronically using LIFESEQ™ database.

DESCRIPTION OF THE INVENTION

Figure 7A:
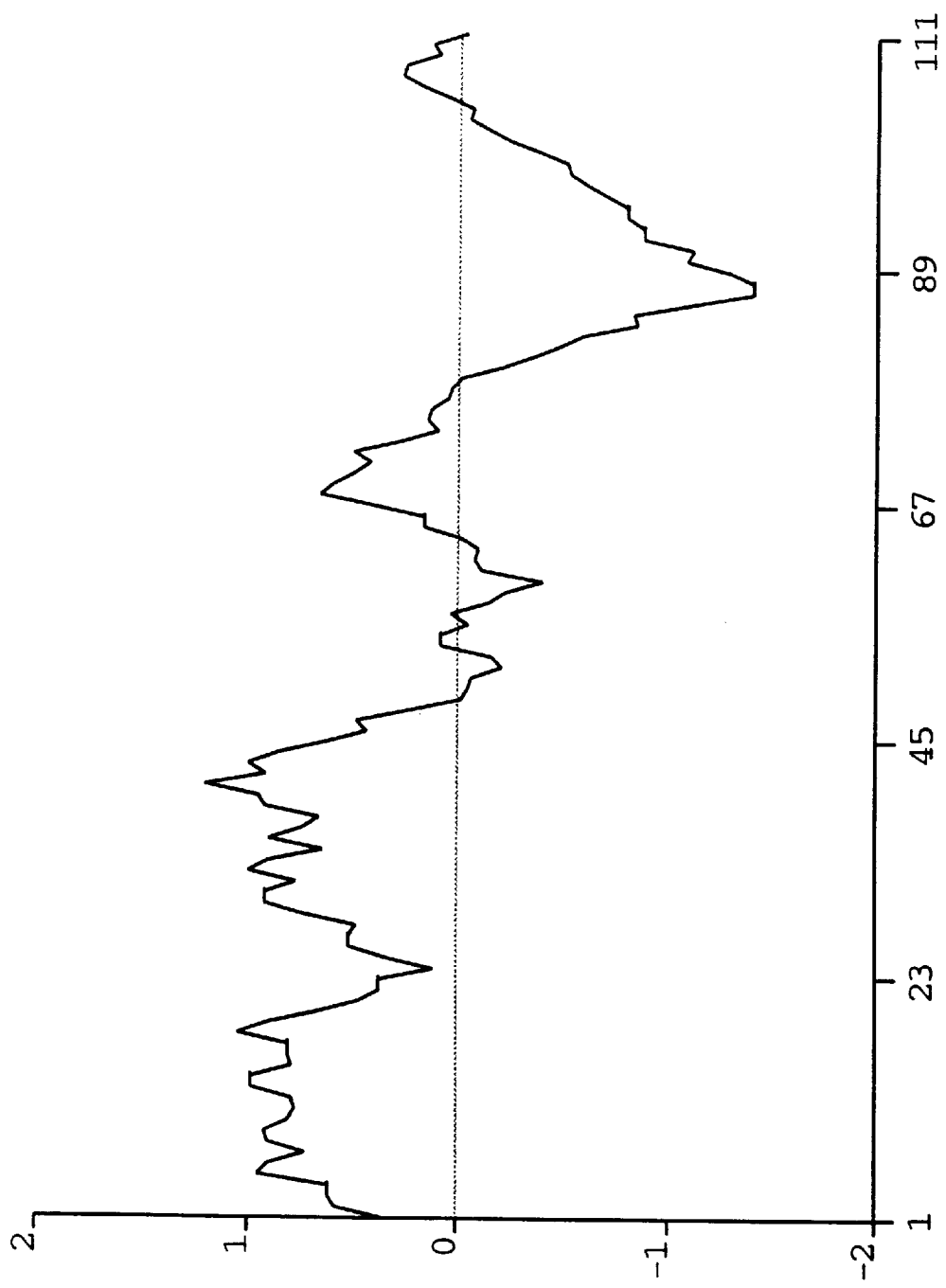
FIGS. 7A and 7B show the hydrophobicity plots for VTAP-1 (SEQ ID NO:1) and mouse GS 15 (SEQ ID NO:8), respectively; the positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

VTAP, as used herein, refers to the amino acid sequences of substantially purified VTAP obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to VTAP, increases or prolongs the duration of the effect of VTAP. Agonists may include proteins, nucleic acids, carbohydrates, or any other molecules which bind to and modulate the effect of VTAP.

An "allele" or "allele sequence", as used herein, is an alternative form of the gene encoding VTAP. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding VTAP, as used herein, include those which deletions, insertions, or substitutions of different nucleotides resulting in a polynucleotide that encodes the same or a functionally equivalent VTAP. Included within this definition are polymorphisms which may or may not be readily detectable using a particular oligonucleotide probe of the polynucleotide encoding VTAP, and improper or unexpected hybridization to alleles, with a locus other than the normal chromosomal locus for the polynucleotide sequence encoding VTAP. The encoded protein may also be "altered" and contain deletions, insertions, or substituents of amino acid residues which produce a silent change and result in a functionally equivalent VTAP. Deliberate amino acid substitutions may be made on the basis of similarity in polarity, charge, solubility, hydrophobicity, hydrophilicity, and/or the amphipathic nature of the residues as long as the biological or immunological activity of VTAP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, aspargine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of VTAP are preferably about 5 to about 15 amino acids in length and retain the biological activity or the immunological activity of VTAP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to VTAP, decreases the amount or the duration of the effect of the biological or immunological activity of VTAP. Antagonists may include proteins, nucleic acids, carbohydrates, antibodies or any other molecules which decrease the effect of VTAP.

As used herein, the term "antibody" refers to intact molecules as well as fragments thereof, such as Fa, F(ab')$_2$, and Fv, which are capable of binding the epitopic determinant. Antibodies that bind VTAP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic VTAP, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding VTAP (SEQ ID NO:1, SEQ ID NO:3, or SEQ ID NO:5) or fragments thereof (e.g., SEQ ID NO:2, SEQ ID NO:4, or SEQ ID NO:6 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding VTAP in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to VTAP or the encoded VTAP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotides sequence resulting in the addition of one or more amino acid residues or nucleotides, respectively, as compared to the naturally occuring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of VTAP. For example, modulation may cause an increase or a decrease in protein activity, binding characteristics, or any other biological, functional or immunological properties of VTAP.

"Nucleic acid sequence", as used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA, as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, for example, a protein "comprising at least a portion of the amino acid sequence of SEQ ID NO:1" encompasses the full-length VTAP-1 and fragments thereof.

The term "sample", as used herein, is used in its broadest sense. A biological sample suspected of containing nucleic acid encoding VTAP, or fragments thereof, or VTAP itself may comprise a bodily fluid, extract from a cell, chromosome, organelle, or membrane isolated from a cell, a cell, genomic DNA, RNA, or cDNA (in solution or bound to a solid support) a tissue, a tissue print, and the like.

The terms "specific binding" or "specifically binding", as used herein, refer to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of VTAP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of new human vesicle transport associated proteins (hereinafter referred to collectively as "VTAP", and individually as VTAP-1, VTAP-2, and VTAP-3), the polynucleotides encoding VTAP, and the use of these compositions for the diagnosis, prevention, or treatment of cancer, and immune, reproductive, and developmental disorders.

Nucleic acids encoding the VTAP-1 of the present invention were first identified in Incyte Clone 1793721 from the prostate tumor cDNA library (PROSTUT05) using a computer search for amino acid sequence alignments. A consensus sequence, SEQ ID NO:2, was derived from the following overlapping and/or extended nucleic acid sequences: Incyte Clones 1793721 (PROSTUT05) and 2674823 (KIDNNOT19).

Nucleic acids encoding the VTAP-2 of the present invention were first identified in Incyte Clone 2607622 from the lung tumor cDNA library (LUNGTUT03) using a computer search for amino acid sequence alignments. A consensus sequence, SEQ ID NO:4, was derived from the following overlapping and/or extended nucleic acid sequences: Incyte Clones 03169 (HMC1NOT01), 988007 (LVENNOT03), 1338893 (COLNTUT03), 1830282 (THP1AZT01), 1911286 (CONNTUT01), 2607662 (LUNGTUT07), 2645022 (OVARTUT03), 2872178 (THYRNOT10), and 3141976 (SMCCNOT02).

Nucleic acids encoding the VTAP-3 of the present invention were first identified in Incyte Clone 2620104 from the epidermal keratinocyte cDNA library (KERANOT02) using a computer search for amino acid sequence alignments. A consensus sequence, SEQ ID NO:6, was derived from the following overlapping and/or extended nucleic acid sequences: Incyte Clones 793405 (PROSTUT03), 1708524 (PROSNOT16), 2124803 (BRSTNOT07), 2414160 (HNT3AZT01), 2583974 (BRAITUT22), and 2620104 (KERANOT02).

Figure 4:
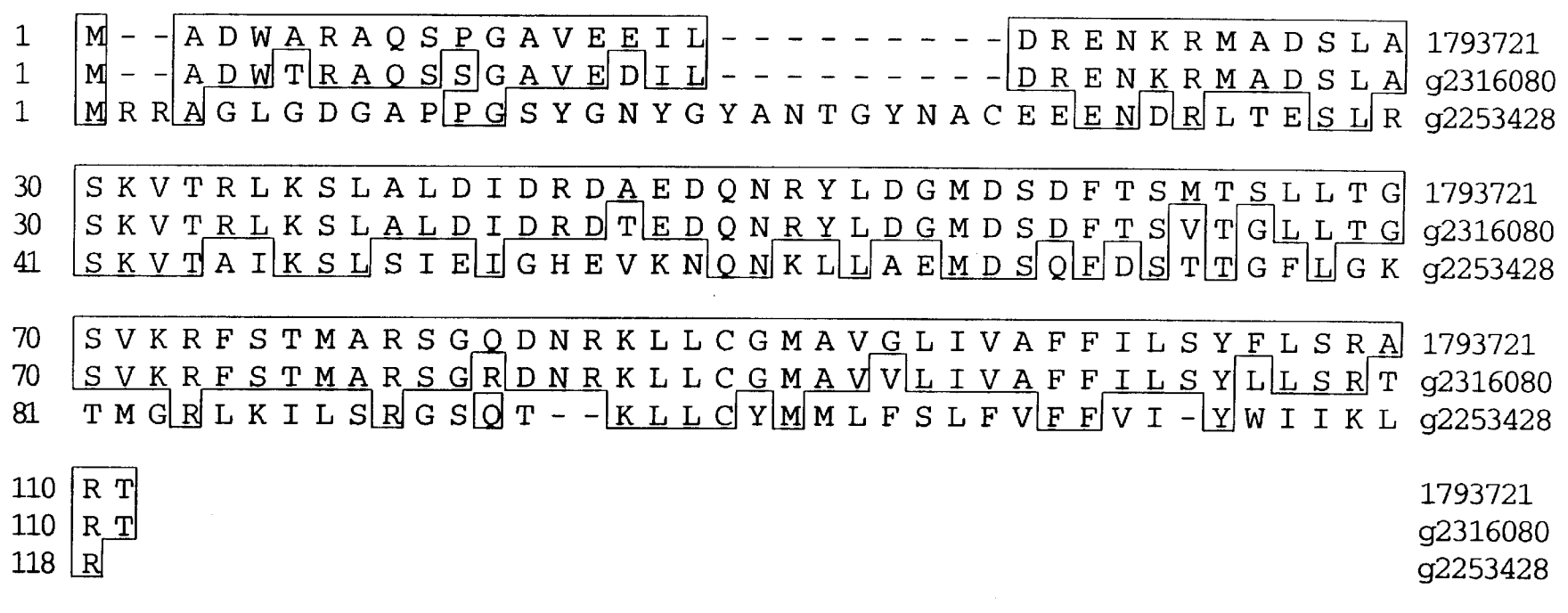
Figure 7B:
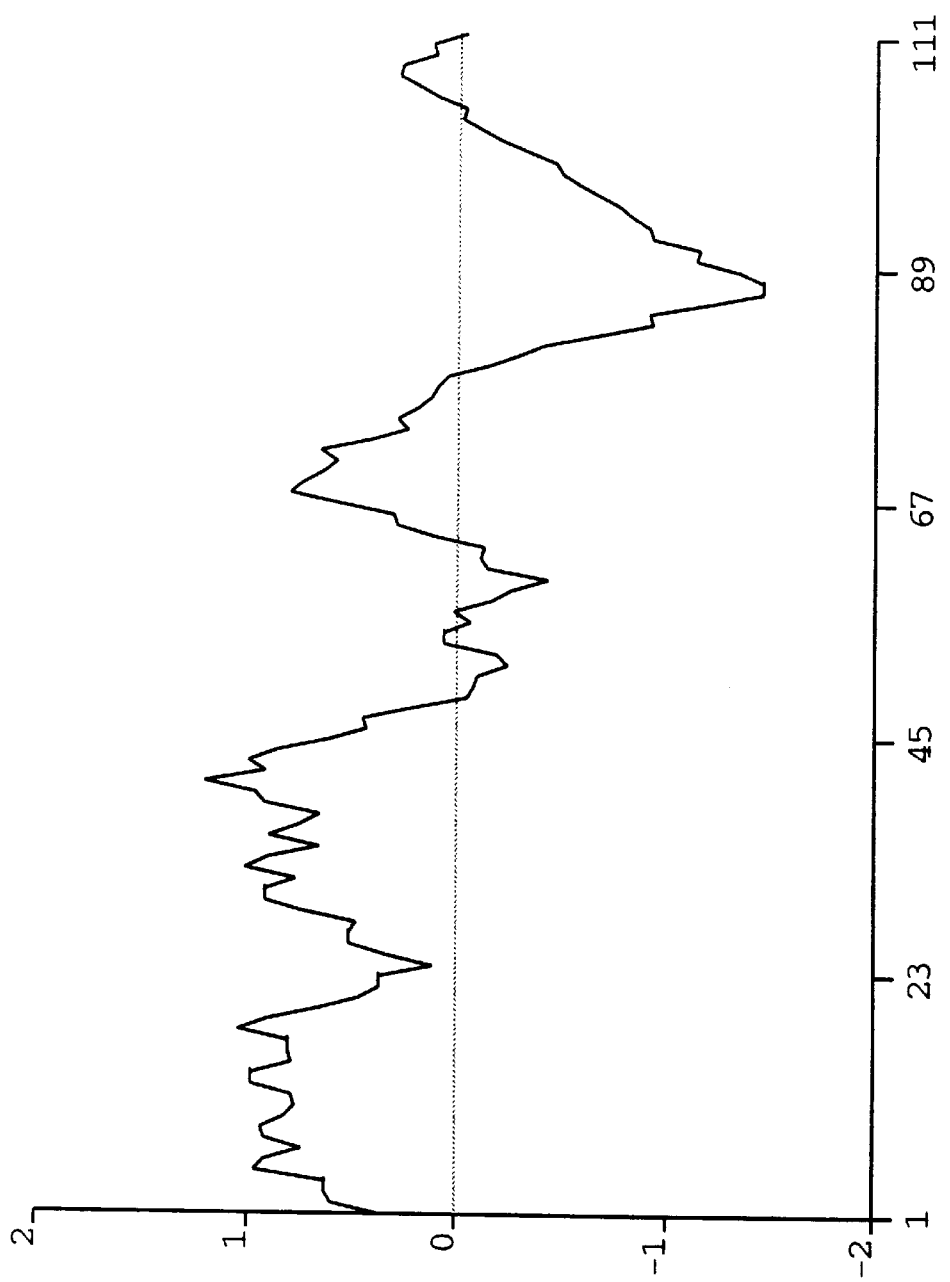

In one embodiment, the invention encompasses a polypeptide comprising the amino acid sequence of SEQ ID NO:1, as shown in FIGS. 1A and 1B. VTAP-1 is 111 amino acids in length and has several potential protein kinase phosphorylation sites for cyclic-AMP/GMP protein kinase at residue $S_{75}$, for casein kinase II at $S_{80}$, for protein kinase C at $S_{70}$, and for tyrosine kinase at $Y_{52}$. As shown in FIG. 4, VTAP-1 has chemical and structural homology with the mouse Golgi SNARE protein, GS 15 (GI 2316080; SEQ ID NO:7) and the mouse mBET1 (GI 2253428; SEQ ID NO:8). In particular, VTAP-1 shares 91% and 35% identity with GS 15 and mBET1, respectively. GS 15 shares all four of the potential protein kinase phosphorylation sites found in VTAP-1. As illustrated by FIGS. 7A and 7B, VTAP-1 and mouse GS 15 have rather similar hydrophobicity plots. In particular, both proteins exhibit a primarily hydrophilic character in the N-terminal and central regions of their structure, and a hydrophobic potential membrane anchor in the C-terminal region. Northern analysis (FIG. 9) shows the expression of this sequence in various libraries, at least 50% of which are immortalized or cancerous and at least 58% of which are from the reproductive system.

Figure 5:
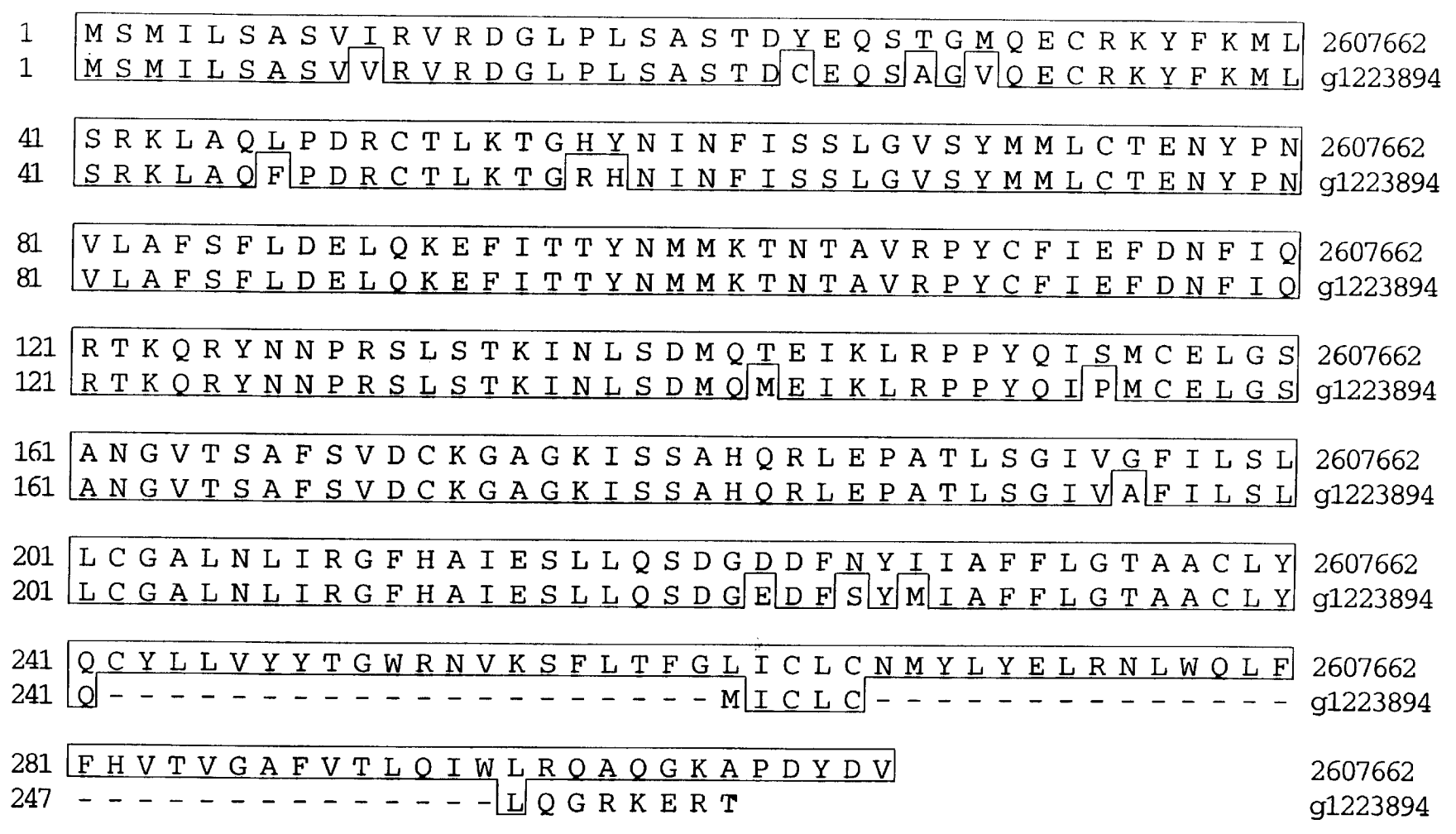
Figure 8A:
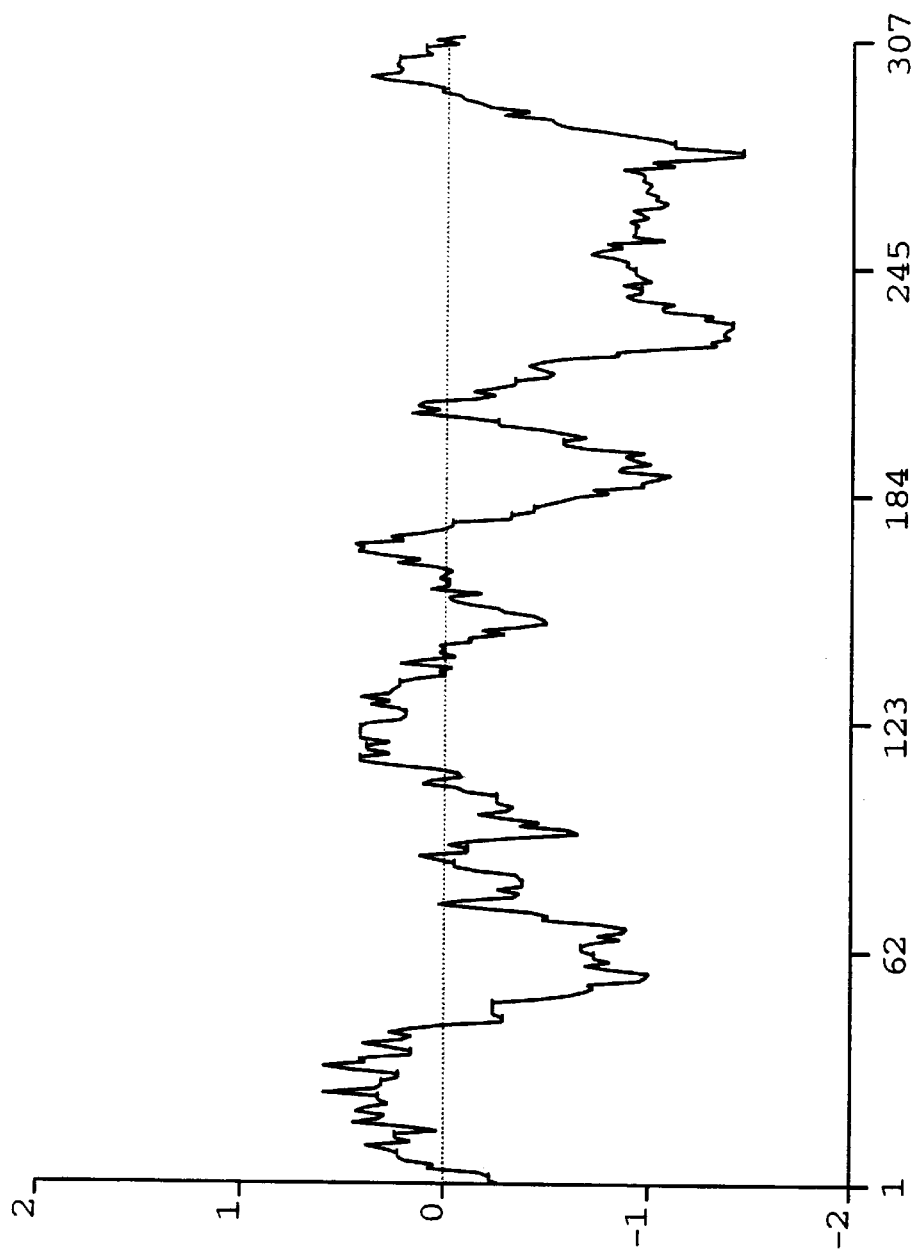
FIGS. 8A and 8B show the hydrophobicity plots for VTAP-2 (SEQ ID NO:3) and rat SEC22 (SEQ ID NO:9), respectively; the positive X axis reflects amino acid position, and the negative Y axis, hydrophobicity (MACDNASIS PRO software).
Figure 8B:
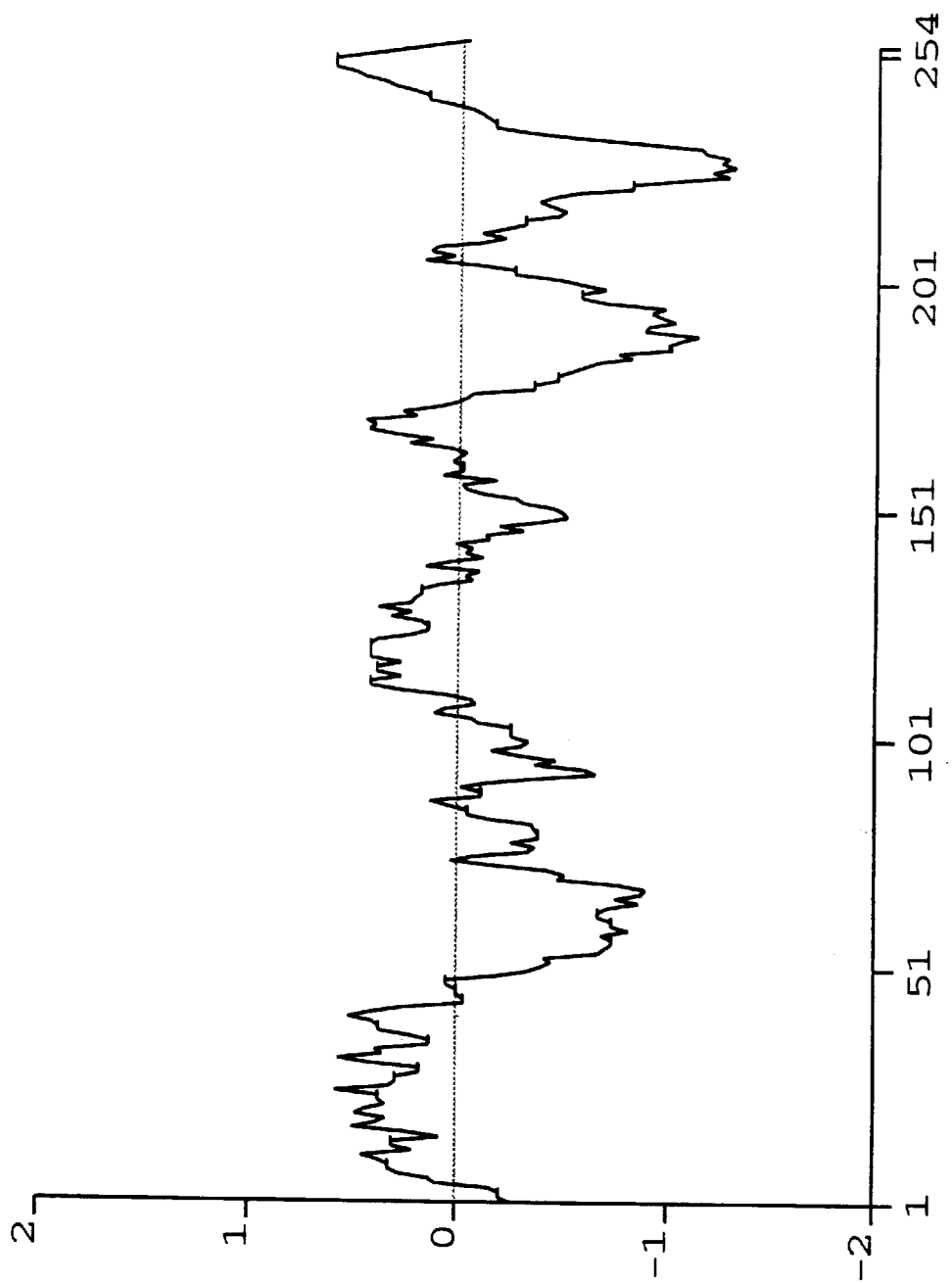

In another embodiment, the invention encompasses a polypeptide comprising the amino acid sequence of SEQ ID NO:3, as shown in FIGS. 2A, 2B, 2C, and 2D. VTAP-2 is 307 amino acids in length and has a potential N-linked glycosylation site at residue $N_{137}$. Potential protein kinase phosphorylation sites are found for casein kinase II at $T_{22}$, $S_{85}$, $S_{154}$, and $S_{220}$, and potential protein kinase C phosphorylation sites are found at $S_{41}$, $T_{52}$, and $S_{133}$. As shown in FIG. 5, VTAP-2 has chemical and structural homology with rat SEC22 (GI 1223894; SEQ ID NO:9). In particular, VTAP-1 and rat SEC22 share 92% homology. VTAP-2 and SEC22 share the N-linked glycosylation site and all of the potential protein kinase phosphorylation sites found in VTAP-2. VTAP-2 differs from SEC22 primarily in the extension of the former at the C-terminal end of the molecule. As illustrated by FIGS. 8A and 8B, VTAP-2 and rat SEC22 have rather similar hydrophobicity plots. Both proteins have similar hydrophilic regions in the N-terminal and central regions of the molecule, and a hydrophobic potential membrane anchoring region at the C-terminus. The additional residues in VTAP-2 at the C-terminal end increase hydrophobicity in this region compared to SEC22. Northern analysis (FIG. 10) shows the expression of this sequence in various libraries, at least 60% of which are immortalized or cancerous, and at least 20% of which involve inflammation of the immune response. Of particular note is the expression of this sequence in cancers of the reproductive system including breast, ovaries, and prostate.

Figure 6:
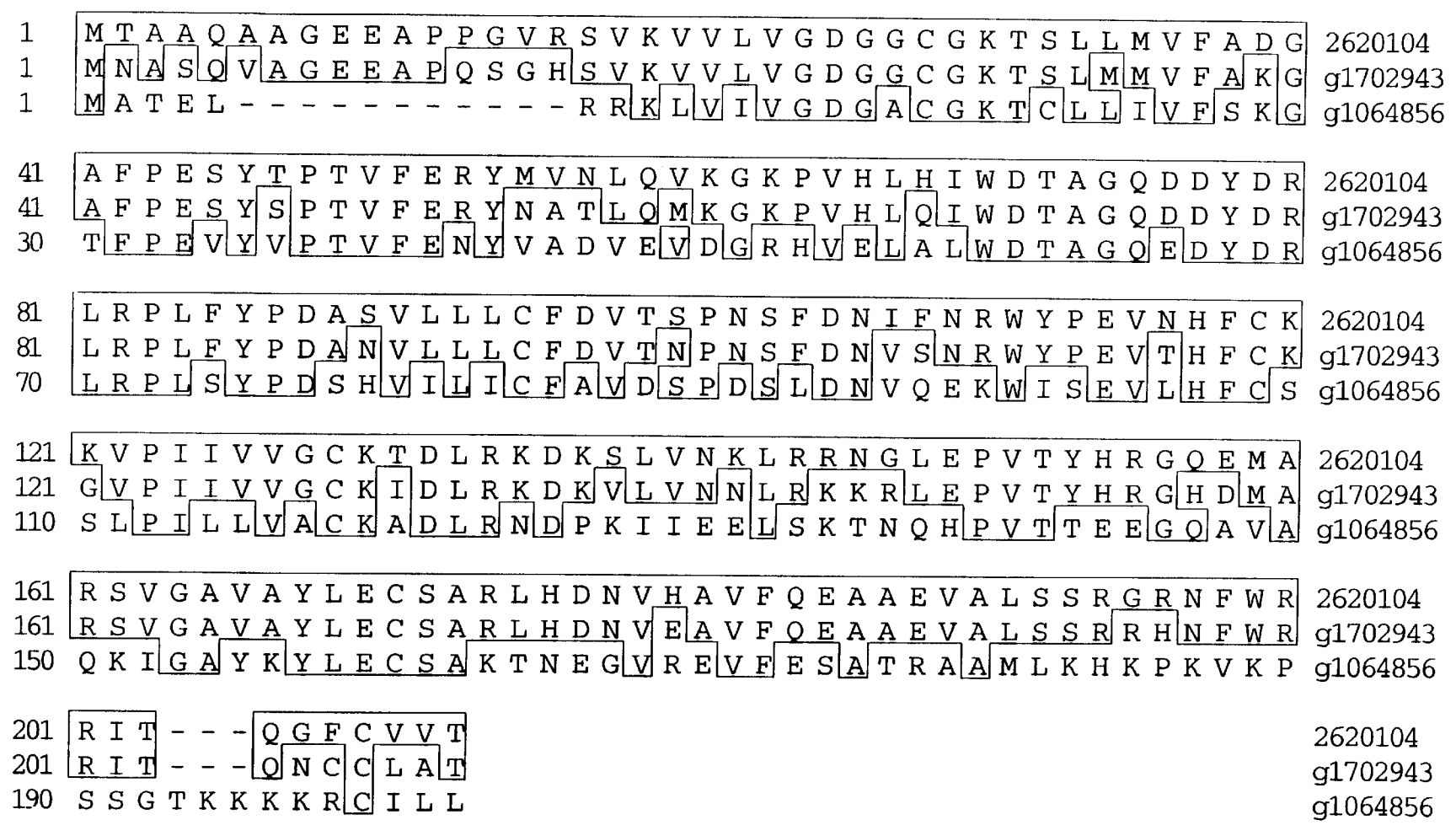

In another embodiment, the invention encompasses a polypeptide comprising the amino acid sequence of SEQ ID NO:5, as shown in FIGS. 3A, 3B, and 3C. VTAP-3 is 210 amino acids in length and has several potential protein kinase phosphorylation sites, for cyclic AMP/GMP protein kinase at $T_{203}$, for casein kinase II at $T_{49}$, for protein kinase C at $S_{17}$, $S_{172}$, and $S_{192}$, and for tyrosine kinase at $Y_{153}$. Four sequence motifs common to GTP-binding proteins are also found in VTAP-3. The ATP/GTP binding site is found at $G_{24}$DGGCGKT, and the three additional sequence motifs involved in GTP binding and hydrolysis are found at $D_{71}$TAGQ, $C_{129}$KTDL, and $E_{170}$CSAR. The CAAX box (prenylation site) for VTAP-3 is found at $C_{207}$VVT. As shown in FIG. 6, VTAP-3 has chemical and structural homology with mouse RhoD (GI 1702943; SEQ ID NO:10) and yeast Rho1 (GI 1064856; SEQ ID NO:11). In particular, VTAP-3 shares 85% and 47% identity with mouse RhoD and yeast Rho1, respectively. The four GTP-binding motifs are similar in all three proteins, and all three proteins exhibit the C-terminal CAAX box. Most of the potential protein kinase phosphorylation sites found in VTAP-3 are also found in RhoD and Rho1. Northern analysis FIG. 11) shows the expression of this sequence in various libraries, at least 60% of which are immortalized or cancerous, and at least 53% of which involve fetal tissues and proliferating cell lines.

The invention also encompasses VTAP variants. A preferred VTAP variant is one having at least 80%, and more preferably at least 90%, amino acid sequence identity to the VTAP amino acid sequence (SEQ ID NO:1, SEQ ID NO:3, or SEQ ID NO:5) and which retains at least one biological, immunological or other functional characteristic or activity of VTAP. A most preferred VTAP variant is one having at least 95% amino acid sequence identity to SEQ ID NO:1, SEQ ID NO:3, or SEQ ID NO:5.

The invention also encompasses polynucleotides which encode VTAP. Accordingly, any nucleic acid sequence which encodes the amino acid sequence of VTAP can be used to produce recombinant molecules which express VTAP. In a particular embodiment, the invention encompasses the polynucleotide comprising the nucleic acid sequence of SEQ ID NO:2 as shown in FIGS. 1A and 1B. In another embodiment, the invention encompasses the polynucleotide sequence comprising the nucleic acid sequence of SEQ ID NO:4 as shown in FIGS. 2A, 2B, 2C, and 2D. In still another embodiment, the invention encompasses the poly-nucleotide sequence comprising the nucleic acid sequence of SEQ ID NO:6 as shown in FIGS. 3A, 3B, and 3C.

It will be appreciated by those skilled in the art that as a result of the degeneracy of the genetic code, a multitude of nucleotide sequences encoding VTAP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring VTAP, and all such variations are to be considered as being specifically disclosed.

Although nucleotide sequences which encode VTAP and its variants are preferably capable of hybridizing to the nucleotide sequence of the naturally occurring VTAP under appropriately selected conditions of stringency, it may be advantageous to produce nucleotide sequences encoding VTAP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding VTAP and its derivatives without altering the encoded amino acid sequences include the production of RNA transcripts having more desirable properties, such as greater half-life, than transcripts produced from the naturally occurring sequence.

The invention also encompasses production of DNA sequences, or fragments thereof, which encode VTAP and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding VTAP or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art may be used to practice any of the embodiments of the invention. The methods may employ such enzymes as the Klenow fragment of DNA polymerase I, SEQUENASE® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding VTAP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circulated by intramolecular ligation and used as a PCR template.

Another method which may be used in capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, the polynucleotide sequences or fragments thereof which encode VTAP may be used in recombinant DNA molecules to direct expression of VTAP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express VTAP.

As will be understood by those of skill in the art, it may be advantageous to produce VTAP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter VTAP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding VTAP may be ligated to a heterologous sequence to encode a fusion protein. For example, to screen peptide libraries for inhibitors of VTAP activity, it may be useful to encode a chimeric VTAP protein that can be recognized by a commercially available antibody. A fusion protein may also be engineered to contain a cleavage site located between the VTAP encoding sequence and the heterologous protein sequence, so that VTAP may be cleaved and purified away from the heterologous moiety.

In another embodiment, sequences encoding VTAP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of VTAP, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Crieghton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of VTAP, or any part thereof, may be altered during direct synthesis and/or combined using chemical methods with sequences from other proteins, or any part thereof, to produce a variant polypeptide.

In order to express a biologically active VTAP, the nucleotide sequences encoding VTAP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding VTAP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding VTAP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding VTAP, vectors based on SV40 or EBV may be used with an appropriate selectable marker.

In bacterial systems, a number of expression vectors may be selected depending upon the use intended for VTAP. For example, when large quantities of VTAP are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding VTAP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisia,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding VTAP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express VTAP. For example, in one such system, *Autographa californica* nuclear polyhedrosis virus (AcNPV) is used as a vector to express foreign genes in *Spodoptera frugiperda* cells or in Trichoplusia larvae. The sequences encoding VTAP may be cloned into a non-essential region of the virus, such as the polyhedrin gene, and placed under control of the polyhedrin promoter. Successful insertion of VTAP will render the polyhedrin gene inactive and produce recombinant virus lacking coat protein. The recombinant viruses may then be used to infect, for example, *S. frugiperda* cells or Trichoplusia larvae in which VTAP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding VTAP may be ligated into an adenovirus transcription/translation complex consisting of the late promoter and tripartite leader sequence. Insertion is a non-essential E1 or E3 region of the viral genome may be used to obtain a viable virus which is capable of expressing VTAP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding VTAP. Such signals include the ATG initiation codon and adjacent sequences. In cases where sequences encoding VTAP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express VTAP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistance clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding VTAP is inserted within a marker gene sequence, transformed cells containing sequence encoding VTAP can be identified by the absence of marker gene function. Alternatively, a marker gene can be placed in tandem with a sequence encoding VTAP under the control of a signal promoter. Expression of the marker gene in response to induction or selection usually indicates expression of the tandem gene as well.

Alternatively, host cells which contain the nucleic acid sequence encoding VTAP and express VTAP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding VTAP can be detected by DNA-DNA or DNA-RNA hybridization or amplification using probes or fragments or fragments of polynucleotides encoding VTAP. Nucleic acid amplification based assays involve the use of oligonucleotides or oligomers based on the sequences encoding VTAP to detect transformants containing DNA or RNA encoding VTAP.

A variety of protocols for detecting and measuring the expression of VTAP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on VTAP is preferred, but a competitive binding assay may be employed. These and other assays are described, among other places, in Hampton, R. et al. (1990; *Serological Methods, a Laboratory Manual,* APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding VTAP include oligolabeling, nick translation, end-labeling or PCR amplification using a labeled nucleotide. Alternatively, the sequences encoding VTAP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison, Wis.); and U.S. Biochemical Corp., (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding VTAP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode VTAP may be designed to contain signal sequences which direct secretion of VTAP through a prokaryotic or eukaryotic cell membrane. Other constructions may be used to join sequences encoding VTAP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle. Wash.). The inclusion of cleavable linker sequences such as those specific for Factor XA or enterokinase (Invitrogen, San Diego, Calif.) between the purification domain and VTAP may be used to facilitate purification. One such expression vector provides for expression of a fusion protein containing VTAP and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263–281) while the enterokinase cleavage site provides a means for purifying VTAP from the fusion protein. A discussion of vectors which contain fusion proteins is provided in Kroll, D. J. et al. (1993; DNA Cell Biol. 12:441–453).

In addition to recombinant production, fragments of VTAP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of VTAP may be chemically synthesized separately and combined using chemical methods to produce the full length molecule.

Therapeutics

Chemical and structural homology exits among VTAP-1 and the vesicle transport proteins, GS15 (GI 2316080) and BET1(GI 2253428) from mouse. In addition, VTAP-1 is expressed in cancerous tissues and immortalized cell lines and tissues associated with the reproductive system. Therefore, VTAP-1 appears to play a role in cancer and reproductive disorders. In particular, increased expression or activity of VTAP-1 appears to be associated with these diseases and disorders.

Therefore, in one embodiment, an antagonist of VTAP-1 may be administered to a subject to prevent or treat cancer. Types of cancer may include, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds VTAP-1 may be used directly as an antagonist or indirectly as a targeting or delivery mechanism for bringing a pharmaceutical agent to cells or tissue which express VTAP-1.

In another embodiment, a vector expressing the complement of the polynucleotide encoding VTAP-1 may also be administered to a subject to treat or prevent cancer including, but not limited to, the types of cancer described above.

In another embodiment, an antagonist VTAP-1 may be administered to a subject to prevent or treat a reproductive disorder. Such disorders may include, but are not limited to, disorders or prolactin production; infertility including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; and disruptions of spermatogenesis, abnormal sperm physiology, cancer of the testis, cancer of the prostate, benign prostatic hyperplasia, prostatitis, carcinoma of the male breast, and gynecomastia.

In another embodiment, a vector expressing the complement of the polynucleotide encoding VTAP-1 may be administered to a subject to treat or prevent a reproductive disorder including, but not limited to, those described above.

Chemical and structural homology exists between VTAP-2 and the vesicle transport protein SEC22 from rat (GI 1223894). In addition, VTAP-2 is expressed in cancerous tissues and immortalized cell lines and tissues associated with inflammation and the immune response. Therefore, VTAP-2 appears to play a role in cancer and immune disorders. In particular, increased expression or activity of VTAP-2 appears to be associated with these diseases and disorders.

Therefore, in one embodiment, an antagonist of VTAP-2 may be administered to a subject to prevent or treat cancer. Types of cancer may include, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, galglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds VTAP-2 may be used directly as an antagonist or indirectly as a targeting or delivery mechanism for bringing a pharmaceutical agent to cells or tissue which express VTAP-2.

In another embodiment, a vector expressing the complement of the polynucleotide encoding VTAP-2 may be administered to a subject to treat or prevent cancer including, but not limited to, the types of cancer described above.

In another embodiment, an antagonist of VTAP-2 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections, and trauma.

In another embodiment, a vector expressing the complement of the polynucleotide encoding VTAP-2 may be administered to a subject to treat or prevent an immune disorder including, but not limited to, those described above.

Chemical and structural homology exists among VTAP-3 and the vesicle transport, GTP-binding proteins from mouse, RhoD (GI 1702943) and yeast, Rho1 (GI 1064856). In addition, VTAP-3 is expressed in cancerous tissues and immortalized cell lines and in fetal tissues and proliferating cell lines. Therefore, VTAP-3 appears to play a role in cancer and developmental disorders. In particular, increased expression or activity of VTAP-3 appears to be associated with cancer, while decreased expression or activity of VTAP-3 appears to be associated with developmental disorders.

In one embodiment VTAP-3, or a fragment or derivative thereof, may be administered to a subject to treat or prevent a development disorder. Such disorders may include, but are not limited to, renal tubular acidosis, anemia, Cushing's syndrome, achondroplastic dwarfism, Duchenne and Becker muscular dystrophy, epilepsy, gonadal dysgenesis, WAGR syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss.

In another embodiment, a vector capable of expressing VTAP-3, or a fragment or a derivative thereof, may also be administered to a subject to treat or prevent a developmental disorder including, but not limited to, those described above.

In still another embodiment, an agonist which modulates the activity of VTAP-3 may also be administered to a subject to treat or prevent a developmental disorder including, but not limited to, those described above.

In another embodiment, an antagonist of VTAP-1 may be administered to a subject to prevent or treat cancer. Types of caner may include, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds VTAP-3 may be used directly as an antagonist or indirectly as a targeting or delivery mechanism for bringing a pharmaceutical agent to cells or tissue which express VTAP-3.

In another embodiment, a vector expressing the complement of the polynucleotide encoding VTAP-3 may be administered to a subject to treat or prevent cancer including, but not limited to, the types of cancer described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of VTAP may be produced using methods which are generally known in the art. In particular, purified VTAP may be used to produce antibodies or to screen libraries of pharmaceutical agents to identify those which specifically bind VTAP.

Antibodies to VTAP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with VTAP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to VTAP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of VTAP amino acids may be fused with those of another protein such as keyhole limpet hemocyanin and antibody produced against the chimeric molecule.

Monoclonal antibodies to VTAP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce VTAP-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for VTAP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between VTAP and its specific antibody. A two-site, monoclonal-based immunoassay utilizing monoclonal antibodies reactive to two non-interfering VTAP epitopes is preferred, but a competitive binding assay may also be employed (Maddox, supra).

In another embodiment of the invention, the polynucleotides encoding VTAP, or any fragment or complement thereof, may be used for therapeutic purposes. In one aspect, the complement of the polynucleotide encoding VTAP may be used in situations in which it would be desirable to block the transcription of the mRNA. In particular, cells may be transformed with sequences complementary to polynucleotides encoding VTAP. Thus, complementary molecules or fragments may be used to modulate VTAP activity, or to achieve regulation of gene function. Such technology is now well known in the art, and sense or antisense oligonucleotides or larger fragments, can be designed from various locations along the coding or control regions of sequences encoding VTAP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding VTAP. These techniques are described both in Sambrook et al. (supra) and in Ausubel et al. (supra).

Genes encoding VTAP can be turned off by transforming a cell or tissue with expression vectors which express high levels of a polynucleotide or fragment thereof which encodes VTAP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding VTAP (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding VTAP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription DNA sequences encoding VTAP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of VTAP, antibodies to VTAP, mimetics, agonists, antagonists, or inhibitors of VTAP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidine, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parental administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of VTAP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example VTAP or fragments thereof, antibodies of VTAP, agonists, antagonists or inhibitors of VTAP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or not toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind VTAP may be used for the diagnosis of conditions or diseases characterized by expression of VTAP, or in assays to monitor patients being treated with VTAP, agonists, antagonists or inhibitors. The antibodies useful for diagnostic purposes may be prepared in the same manner as those described above for therapeutics. Diagnostic assays for VTAP include methods which utilize the antibody and a label to detect VTAP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring VTAP are known in the art and provide a basis for diagnosing altered or abnormal levels of VTAP expression. Normal or standard values for VTAP expression are established by combining body fluids or cell extracts taken from normal mammalian subjects, preferably human, with antibody to VTAP under conditions suitable for complex formation. The amount of standard complex formation may be quantified by various methods, but preferably by photometric means. Quantities of VTAP expressed in subject, control and disease, samples from biopsied tissues are compared with the standard values. Deviation between standard and subject values establishes the parameters for diagnosing disease.

In another embodiment of the invention, the polynucleotides encoding VTAP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of VTAP may be correlated with disease. The diagnostic assay may be used to distinguish between absence, presence, and excess expression of VTAP, and to monitor regulation of VTAP levels during therapeutic intervention.

In one aspect, hybridization with PCR probes which are capable of detecting polynucleotide sequences, including genomic sequences, encoding VTAP or closely related molecules, may be used to identify nucleic acid sequences which encode VTAP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding VTAP, alleles, or related sequences.

Probes may also be used for the detection of related sequences, and should preferably contain at least 50% of the nucleotides from any of the VTAP encoding sequences. The hybridization probes of the subject invention may be DNA or RNA and derived from the nucleotide sequence of SEQ ID NO:2, SEQ ID NO:4, or SEQ ID NO:6 or from genomic sequence including promoter, enhancer elements, and introns of the naturally occurring VTAP.

Means for producing specific hybridization probes for DNAs encoding VTAP include the cloning of nucleic acid sequences encoding VTAP or VTAP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding VTAP may be used for the diagnosis of conditions or disorders which are associated with expression of VTAP. Examples of such conditions or disorders include cancer, such as adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections, and trauma; reproductive disorders such as disorders of prolactin production; infertility including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; and disruptions of spermatogenesis, abnormal sperm physiology, cancer of the testis, cancer of the prostate, benign prostatic hyperplasia, prostatitis, carcinoma of the male breast, and gynecomastia; and developmental disorders such as renal tubular acidosis, anemia, Cushing's syndrome, achondroplastic dwarfism, Duchenne and Becker muscular dystrophy, epilepsy, gonadal dysgenesis, WAGR syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss. The polynucleotide sequences encoding VTAP may be used in Southern or northern analysis, dot blot, or other membrane-based technologies; in PCR technologies; or in dipstick, pin, ELISA assays or microarrays utilizing fluids or tissues from patient biopsies to detect altered VTAP expression. Such qualitative or quantitative methods are well known in the art.

In a particular aspect, the nucleotide sequences encoding VTAP may be useful in assays that detect activation or induction of various cancers, particularly those mentioned above. The nucleotide sequences encoding VTAP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding VTAP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of VTAP, a normal or standard profile for expression is established. This may be accomplished by combining body fluids or cell extracts taken from normal subjects, either animal or human, with a sequence, or a fragment thereof, which encodes VTAP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding VTAP may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of VTAP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5' or 3' sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode VTAP may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:27–134, and Trask, B. J. (1991) Trends Genet. 7:149–154.

Fluorescent in situ hybridization (FISH as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding VTAP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, VTAP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between VTAP and the agent being tested, may be measured.

Another technique for drug screening which may be used provides for high throughput screening of compounds having suitable binding affinity to the protein of interest as described in published PCT application WO84/03564. In this method, as applied to VTAP, large numbers of different small test compounds are synthesized on a solid substrate, such as plastic pins or some other surface. The test compounds are reacted with VTAP, or fragments thereof, and washed. Bound VTAP is then detected by methods well known in the art. Purified VTAP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding VTAP specifically compete with a test compound for binding VTAP. In this manner, the antibodies can be used to detect the presence of any peptide which shares one or more antigenic determinants with VTAP.

In additional embodiments, the nucleotide sequences which encode VTAP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

PROSTUTO5

The Prostut05 cDNA library was constructed from tumor prostate tissue removed from a 69-year-old male. The pathology report indicated an adenocarcinoma (Gleason grade 3+4). The patient presented with elevated prostate specific antigen (PSA). Family history included congestive heart failure in the father, benign hypertension in the mother, and benign hypertension, multiple myeloma, hyperlipidemia, and rheumatoid arthritis in siblings.

KERANOTO2

The KERANTO2 cDNA library was constructed from a normal epidermal keratinocyte (NHEK) primary cell line acquired from Clonetics (San Diego, Calif.; catalog #CC-2501, specimen #: 2199), obtained from a 30 year-old black female undergoing breast reduction surgery. Patient history included tobacco and alcohol use and elevated blood pressure. Epidermal keratinocytes were isolated from the resected tissue and allowed to proliferate before cryopreservation.

For both libraries, the frozen tissue was homogenized and lysed using a Brinkmann Homogenizer Polytron PT-3000 (Brinkmann Instruments, Westbury, N.J.). The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. RNA was extracted with phenol chloroform pH 4.0, precipitated using 0.3 M sodium acetate and 2.5 volumes of ethanol, resuspended in DEPC-treated water and DNase treated at 37° C. RNA extraction and precipitation were repeated as before. The RNA was then isolated using the QIAGEN OLIGOTEX kit (QIAGEN Inc.; Chatsworth, Calif.) and used to construct the cDNA library.

The RNA was handled according to the recommended protocols in the SuperScript Plasmid System for cDNA Synthesis and Plasmid Cloning (catalog #18248-013; Gibco/BRL, Gaithersburg, Md.). cDNAs were fractionated on a Sepharose GL4B column (catalog #275105, Pharmacia), and those cDNAs exceeding 400 bp were ligated into PSPORT1. The plasmid PSPORT1 was subsequently transformed into DH5a™ competent cells (Cat. #18258-012, Gibco/BRL).

LUNGTUT07

The LUNGTUT07 cDNA library was constructed from cancerous lung tissue obtained from an 50-year-old Caucasian male (specimen #0782A; Mayo Clinic, Rochester, Minn.) during a segmental lung resection following diagnosis of malignant neoplasm of the upper lobe of the lung. Pathology report indicated an invasive grade 4 squamous cell adenocarcinoma forming a subpleural mass which puckered the underlying pleura. The tumor did not infiltrate the pleura. Reactive mesothelial cells and fibrin were present at the right lower lobe or pleural implant. The bronchial margin, multiple (7) intrapulmonary peribronchial lymph nodes, the superior mediastinal lymph nodes were negative for tumor. In addition, multiple inferior mediastinal lymph nodes were negative for tumor. The patient presented with a respiratory anomaly and chest pain. Patient family history included malignant skin melanoma in the mother and a sibling.

The frozen tissue was homogenized and lysed in Trizol reagent (1 gm tissue/10 ml Trizol; Cat. #10296-028; Gibco/BRL), a monoplastic solution of phenol and guanidine isothiocyanate, using a Brinkmann Homogenizer Polytron PT-3000 (Brinkmann Instruments, Westbury, N.Y.). After a brief incubation on ice, chloroform was added (1:5 v/v) and the lysate was centrifuged. The upper chloroform layer was removed to a fresh tube, and the RNA extracted with isopropanol, resuspended in DEPC-treated water, and DNase treated for 25 min at 37° C. The RNA was re-extracted once with acid phenol-chloroform pH 4.7 and precipitated using 0.3M sodium acetate and 2.5 volumes ethanol. The mRNA was then isolated using the Qiagen Oligotex kit (QIAGEN, Inc., Chatsworth, Calif.) and used to construct the cDNA library.

The mRNA was handled according to the recommended protocols in the SuperScript Plasmid System for cDNA Synthesis and Plasmid Cloning (Cat. #18248-013, Gibco/BRL). The cDNAs were fractionated on a Sepharose CL4B column (Cat. #275105-01; Pharmacia), and those cDNAs exceeding 400 bp were ligated into pINCY 1. The plasmid pINCY 1 was subsequently transformed into DH5a™ competent cells (Cat. #18258-012; Gibco/BRL).

II Isolation and Sequencing of cDNA Clones

Plasmid DNA was released from the cells and purified using the REAL Prep 96 Plasmid Kit (Catalog #26173; QIAGEN, Inc.). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) the cultures were incubated for 19 hours after the wells were inoculated and then lysed with 0.3 ml of lysis buffer; and 3) following isopropanol precipitation, the plasmid DNA pellet was resuspended in 0.1 ml of distilled water. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S. F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J. Mol. Evol.* 36:290–300; Altschul, S. F. et al. (1990) *J. Mol. Evol.* 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding VTAP occurs. Abundance and percent abundance are also reported. Abundance directly reflects the number of times a particular transcript is represented in a cDNA library, and percent abundance is abundance divided by the total number of sequences examined in the cDNA library.

V Extension of VTAP Encoding Polynucleotides

The nucleic acid sequence of the Incyte Clones 1793721, 2607662, and 2620104 were used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 1 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent *E. coli* cells (in 40 μl of appropriate media) were transformed with 3 μl of ligation mixture and cultured in 80 μl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, SEQ ID NO:4, or SEQ ID NO:6 is used to obtain 5'

VI Labeling and Use of Individual Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Bioscience), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the VTAP-encoding sequence, or any part thereof, is used to decrease or inhibit expression of naturally occurring VTAP. Although use of oligonucleotides comprising from about 15 to about 30 base-pairs is described, essentially the same procedure is used with smaller or larger sequences fragments. Appropriate oligonucleotides are designed using Oligo 4.06 software and the coding sequence of VTAP, SEQ ID NO:1, SEQ ID NO:3, or SEQ ID NO:5. To inhibit transcription, a complementary oligonucleotide is designed from the most unique 5' sequence and used to prevent promoter binding to the coding sequence. To inhibit translation, a complementary oligonucleotide is designed to prevent ribosomal binding to the VTAP-encoding transcript.

IX Expression of VTAP

Expression of VTAP is accomplished by subcloning the cDNAs into appropriate vectors and transforming the vectors into host cells. In this case, the cloning vector is also used to express VTAP in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcriptase and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of VTAP into the bacterial growth media which can be used directly in the following assay for activity.

X Demonstration of VTAP Activity

VTAP-1

VTAP-1 activity may be assayed by the ability of BET1-like proteins to restore cell viability in yeast lacking the Ypt1 protein, a GTP-binding protein essential for ER-Golgi protein transport and cell growth in yeast (Dascher et al., supra). YPT1 expression and cell growth is suppressed in the GAL10-YPT1 strain of yeast when they are exposed to glucose medium for 12 hours. GAL10-YPT1 yeast cells are therefore transfected with the gene encoding VTAP-1, grown in media containing glucose and compared to untransfected GAL10-YPT1 cells. Cell growth is determined by the increase in cell number over 12 to 24 hours. The rate of cell growth of VTAP-GAL10-YPT1 cells compared to GAL10-YPT1 cells is proportional to the activity of VTAP-1 in the former cells.

VTAP-2

VTAP-2 activity may be measured by the specific binding of VTAP-2 to ER in human COS cells transfected with VTAP-2 (Hay et al., supra). Human COS fibroblasts are transfected with VTAP-2 containing a c-myc amino-terminal tag. VTAP-2 is localized and quantitated by double-label immunofluoresence microscopy using anti-myc monoclonal antibody to detect and quantitate VTAP-2 and anti-calnexin antiserum to stain ER. The amount of anti-myc immunofluoresence found is proportional to the activity of VTAP-2 present.

VTAP-3

VTAP-3 activity may be assayed by the binding and hydrolysis of GTP. Purified VTAP-3 is incubated in a suitable buffer with $H^3$-labeled GTP and incubated at 37° C. for a suitable period of time. Aliquots of the reaction are removed, acidified with trichloroacetic acid and neutralized. The reaction products are separated by electrophoresis, and the GDP spot is cut out and counted in a liquid scintillation radioisotope counter. The amount of radioactivity recovered is proportional to the activity (GTPase) of VTAP-3 in the assay.

XI Production of VTAP Specific Antibodies

VTAP that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc.) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring VTAP Using Specific Antibodies

Naturally occurring or recombinant VTAP is substantially purified by immunoaffinity chromatography using antibodies specific for VTAP. An immunoaffinity column is constructed by covalently coupling VTAP antibody to an activated chromatographic resin, such as CNBr-activated Sepharose (Pharmacia & Upjohn). After the coupling, the resin is blocked and washed according to the manufacturer's instructions.

Media containing VTAP is passed over the immunoaffinity column, and the column is washed under conditions that allow the preferential absorbance of VTAP (e.g., high ionic strength buffers in the presence of detergent). The column is eluted under conditions that disrupt antibody/VTAP binding (e.g., a buffer of pH 2–3 or a high concentration of a chaotrope, such as urea or thiocyanate ion), and VTAP is collected.

XIII Identification of Molecules Which Interact with VTAP

VTAP or biologically active fragments thereof are labeled with $^{125}I$ Bolton-Hunter reagent (Bolton et al. (1973) Biochem. J. 133: 529). Candidate molecules previously arrayed in the wells of multi-well plate are incubated with the labeled VTAP, washed and any wells with labeled VTAP complex are assayed. Data obtained using different concentrations of VTAP are used to calculate values for the number, affinity, and association of VTAP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated or purified polypeptide selected form the group consisting of:
   (a) a polypeptide comprising the sequence set forth in SEQ ID No:3,
   (b) a polypeptide comprising the sequence set forth in SEQ ID No:1, and
   (c) a polypeptide comprising a sequence that is at least 95% identical to the sequence set forth in SEQ ID No:1, wherein said polypeptide mediates vesicle transport activity.

2. A composition comprising the polypeptide of claim 1 in conjunction with a suitable carrier.

3. A method for screening a library of molecules for a molecule which specifically binds the protein of claim 1, the method comprising:
   (a) combining the protein of claim 1 with the library of molecules under conditions suitable to allow complex formation, and
   (b) detecting complex formation, wherein the presence of the complex identifies a molecule which specifically binds the protein.

4. The method of claim 3 wherein the library of molecules is selected from the group consisting of DNA molecules, RNA molecules, agonists, antagonists, carbohydrates, antibodies, inhibitors, peptides, peptide nucleic acids, mimetics, and pharmaceutical agents.

5. A method of purifying a molecule or compound which specifically binds the polypeptide of claim 1 from a sample containing the molecule or compound, the method comprising:
   a) combining the polypeptide of claim 1 with the sample under conditions to allow specific binding;
   b) recovering the polypeptide bound to the molecule or compound; and
   c) separating the polypeptide from the molecule or compound, thereby obtaining purified molecule or compound.

6. A method of making a polyclonal antibody, the method comprising:
   a) immunizing an animal with the polypeptide of claim 1 under conditions to elicit an antibody response;
   b) isolating animal antibodies; and
   c) screening the isolated antibodies with the polypeptide thereby identifying a polyclonal antibody that binds specifically to the polypeptide.

7. A method of making a monoclonal antibody, the method comprising:
   a) immunizing an animal with the polypeptide of claim 1 under conditions to elicit an antibody response;
   b) isolating antibody producing cells from the animal;
   c) fusing the antibody producing cells with immortalized cells in culture to form monoclonal antibody-producing hybridoma cells;
   d) culturing the hybridoma cells; and
   e) isolating from the culture monoclonal antibodies which bind specifically to the polypeptide.

* * * * *

UNITED STATES PATENT AND TRADEMARK OFFICE
CERTIFICATE OF CORRECTION

PATENT NO. : 6,200,790 B1
DATED : March 13, 2001
INVENTOR(S) : Jennifer L. Hillman, Preeti Lal, Purvis Shah, Neil C. Corley It is certified that error appears in the above-identified patent and that said Letters Patent is hereby corrected as shown below:

Column 57, claim 1,
Line 2, delete "form the" and insert -- from the -- ;

Signed and Sealed this

Fourth Day of September, 2001

*Attest:*

*Attesting Officer*

NICHOLAS P. GODICI
*Acting Director of the United States Patent and Trademark Office*